(12) United States Patent
Goda et al.

(10) Patent No.: US 9,622,923 B2
(45) Date of Patent: Apr. 18, 2017

(54) ABSORBENT BODY IN ABSORBENT ARTICLE AND METHOD FOR PRODUCING THE SAME

(71) Applicant: UNICHARM CORPORATION, Ehime (JP)

(72) Inventors: Hiroki Goda, Kagawa (JP); Shinichi Ishikawa, Kagawa (JP); Kengo Ochi, Kagawa (JP); Koichiro Mitsui, Kagawa (JP); Masashi Nakashita, Kagawa (JP); Satoru Tange, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 14/431,744

(22) PCT Filed: Oct. 17, 2013

(86) PCT No.: PCT/JP2013/078136
§ 371 (c)(1),
(2) Date: Mar. 26, 2015

(87) PCT Pub. No.: WO2014/069241
PCT Pub. Date: May 8, 2014

(65) Prior Publication Data
US 2015/0223999 A1 Aug. 13, 2015

(30) Foreign Application Priority Data
Oct. 31, 2012 (JP) .................................. 2012-241330

(51) Int. Cl.
*A61F 13/15* (2006.01)
*A61F 13/53* (2006.01)
*A61F 13/534* (2006.01)

(52) U.S. Cl.
CPC ........ *A61F 13/53* (2013.01); *A61F 13/15634* (2013.01); *A61F 13/15658* (2013.01);
(Continued)

(58) Field of Classification Search
None
See application file for complete search history.

(56) References Cited

U.S. PATENT DOCUMENTS 5,429,788 A * 7/1995 Ribble ................ A61F 13/5323
264/113
5,750,066 A 5/1998 Vonderhaar et al.
(Continued)

FOREIGN PATENT DOCUMENTS

EP 2 184 042 A2 5/2010
EP 2 184 042 A3 12/2010
(Continued)

OTHER PUBLICATIONS

International Search Report from corresponding PCT application No. PCT/JP2013/078136 dated Jan. 21, 2014 (4 pgs).
(Continued)

*Primary Examiner* — Mary F Theisen
(74) *Attorney, Agent, or Firm* — Brinks Gilson & Lione

(57) ABSTRACT

An absorbent body in absorbent articles that causes exudates to disperse in a planar direction and a method of producing the same. The absorbent body has an absorbent core material covered with a cover sheet. The core material has a mass per unit area of 650 g/m$^2$ or less and includes a first liquid absorbent layer containing hydrophilic fibers and superabsorbent polymer particles in a mixed state and a second liquid absorbent layer containing the hydrophilic fibers but none of the superabsorbent polymer particles, wherein the first liquid absorbent layer and the second liquid absorbent layer are overlap with each other and the hydrophilic fibers are in contact with each other between the first liquid absorbent layer and the second liquid absorbent layer.

4 Claims, 16 Drawing Sheets

(52) U.S. Cl.
CPC .... *A61F 13/534* (2013.01); *A61F 2013/5307* (2013.01); *A61F 2013/530496* (2013.01); *A61F 2013/530532* (2013.01)

(56) References Cited

U.S. PATENT DOCUMENTS

| | | | |
|---|---|---|---|
| 5,821,179 | A | 10/1998 | Masaki et al. |
| 5,919,178 | A | 7/1999 | Widlund |
| 2003/0073968 | A1* | 4/2003 | Driskell ............ A61F 13/15577 604/368 |
| 2003/0195485 | A1 | 10/2003 | Rangachari et al. |
| 2003/0234468 | A1 | 12/2003 | Rangachari et al. |
| 2005/0267427 | A1 | 12/2005 | Hanao et al. |
| 2006/0069367 | A1 | 3/2006 | Waksmundzki et al. |
| 2011/0297080 | A1* | 12/2011 | Pastrello ................ B05B 7/144 118/301 |
| 2012/0041406 | A1* | 2/2012 | Alkmin ............ A61F 13/15626 604/383 |
| 2012/0280434 | A1* | 11/2012 | Hoshika ............ A61F 13/15658 264/517 |
| 2012/0312463 | A1* | 12/2012 | Ogasawara ....... A61F 13/15658 156/245 |
| 2013/0023845 | A1 | 1/2013 | Goda et al. |
| 2013/0025795 | A1 | 1/2013 | Ukegawa et al. |

FOREIGN PATENT DOCUMENTS

| | | |
|---|---|---|
| JP | 08-337954 | 12/1996 |
| JP | 9-503691 | 4/1997 |
| JP | 10-500325 | 1/1998 |
| JP | 11-318982 | 11/1999 |
| JP | 2003-515467 A | 5/2003 |
| JP | 2004-065716 | 3/2004 |
| JP | 2006-115999 | 5/2006 |
| JP | 2006-181355 | 7/2006 |
| JP | 2011-177279 | 9/2011 |
| JP | 2011-212290 | 10/2011 |
| WO | WO 2012/035787 A1 | 3/2012 |

OTHER PUBLICATIONS

European extended Search Report from corresponding European application No. 13852031.7 dated Jun. 17, 2016 (9 pgs).

* cited by examiner

FIG.4
(a)
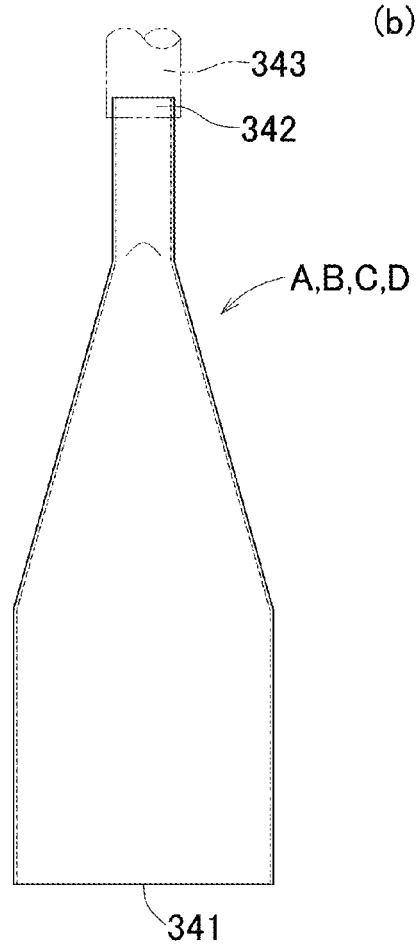
(b)
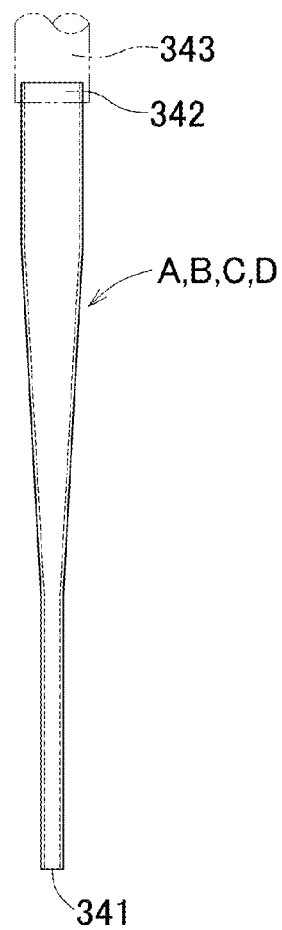
(c)
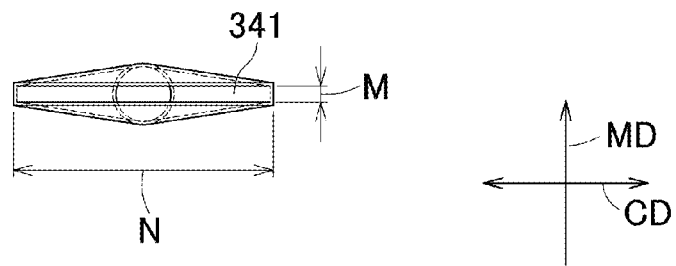

500 μm

ABSORBENT BODY IN ABSORBENT ARTICLE AND METHOD FOR PRODUCING THE SAME

RELATED APPLICATION

This application is a 35 U.S.C. §371 national phase filing of International Patent Application No. PCT/JP2013/078136, filed Oct. 17, 2013, through which and to which priority is claimed under 35 U.S.C. §119 to Japanese Patent Application No. 2012-241330, filed Oct. 31, 2012, the complete disclosure of which are hereby expressly incorporated herein by reference.

TECHNICAL FIELD

The present invention relates to absorbent bodies suitable to be used for absorbent articles such as disposable diapers and sanitary napkins and to a method for producing the same.

BACKGROUND

Absorbent body used for the absorbent articles such as disposable diapers and sanitary napkins are known and it is also known to use water-absorbent fibers such as fluff pulp and super absorbent polymer particles (abbreviated as SAP) for the absorbent bodies.

For example, according to method and apparatus for producing an absorbent body disclosed in Patent Literature 1 (H08-337954 A), fluff pulp is fed into air flowing in one direction and water-absorbent polymer particles are supplied into this air flow to obtain an absorbent body containing the water-absorbent polymer particles evenly dispersed in the fluff pulp.

Method of distributing superabsorbent materials in a fibrous matrix in the form of a bilayer disclosed in Patent Literature 2 (P 2003-515467 A) makes it possible to obtain an absorbent body including a first fibrous layer having a first layer thickness, a first superabsorbent material containing layer combined with the first fibrous layer, a second fibrous layer lapping over the first fibrous layer and having a second layer thickness, and a second superabsorbent material containing layer combined with the second fibrous layer.

CITATION LIST

Patent Literature

{PTL 1}: H-08-337954 A
{PTL 2}: P 2003-515467 A

SUMMARY

Technical Problem

For absorbent body being a mixture of hydrophilic fibers such as fluff pulp with superabsorbent polymer particles both conveyed by air flow, when the superabsorbent polymer particles absorb body exudates such as urine and swell, the hydrophilic fibers which had been laid in a plane orthogonal to a thickness direction of the absorbent body in the production step might change the initial orientation thereof so as to extend in a thickness direction of the absorbent body. Such change of the orientation makes it difficult for the body exudates which could otherwise disperse in a planar direction through the hydrophilic fibers to disperse in the planar direction and, in consequence, the body exudates might stay in a central region in a longitudinal direction as well as in a transverse direction of the absorbent body and the absorbent article put on a wearer's body may create a discomfort feeling against the wearer.

Also the absorbent body obtained by the method disclosed in Patent Literature 2 includes the superabsorbent material in the fibrous layer and swelling of the superabsorbent material causes some fibers in the fibrous layer to change the orientation thereof so as to extend in the thickness direction of the absorbent body. Such change of the orientation makes it difficult for the body exudates to disperse in the planar direction.

An object of the present invention is to improve the known absorbent body so that, in an absorbent body including hydrophilic fibers and superabsorbent polymer particles, body exudates may disperse in a planar direction even after the superabsorbent polymer particles have absorbed the body exudates and swollen.

Solution to Problem

The present invention to solve the problem set forth above includes a first aspect of the invention relating to an absorbent body for the absorbent articles and a second aspect of the invention relating to a method for producing the absorbent body.

The first aspect relates to an absorbent body for an absorbent article including an absorbent core material containing therein hydrophilic fibers and superabsorbent polymer particles and covered with at least partially liquid-permeable cover sheet.

In this absorbent body, the first aspect includes the core material having a mass per unit area of 650 $g/m^2$ or less and containing hydrophilic fibers ranging of 150 to 400 $g/m^2$ and superabsorbent polymer particles in a range of 150 to 350 $g/m^2$ wherein a first liquid absorbent layer in which the hydrophilic fibers and the superabsorbent polymer particles are mixed with each other and a second liquid absorbent layer containing the hydrophilic fibers but not containing the superabsorbent polymer particles overlap each other in a thickness direction of the core material and the hydrophilic fibers are in contact with each other between the first liquid absorbent layer and the second liquid absorbent layer.

The second aspect relates to a method for producing the absorbent body for the absorbent article including the absorbent core material containing therein hydrophilic fibers and superabsorbent polymer particles and covered with at least partially liquid-permeable cover sheet.

In the method for producing the absorbent body, the second aspect includes in a step for forming a first liquid absorbent layer containing the hydrophilic fibers and the superabsorbent polymer particles in a mixed state and a second liquid absorbent layer containing the hydrophilic fibers but none of the superabsorbent polymer particles so that these two liquid absorbent layers may overlap with each other on a support running in a machine direction, the hydrophilic fibers are dispersed toward the support within a chamber partially covering the support and the superabsorbent polymer particles are dispersed toward the support from an opening of a dispersing pipe set at least one of inside and outside the chamber wherein a distance dimension between the dispersing pipe set inside the chamber is in a range of 5 to 20 mm and a distance dimension between the dispersing pipe set outside the chamber and the support is in a range of 5 to 100 mm.

Advantageous Effects of Invention

In the absorbent body in the absorbent articles according to the first aspect of the present invention, the core material includes the first liquid absorbent layer and the second liquid absorbent layer. The first liquid absorbent layer contains the superabsorbent polymer particles and the hydrophilic fibers in a mixed state and the second liquid absorbent layer contains the hydrophilic fibers but none of the superabsorbent polymer particles. Between the first liquid absorbent layer and the second liquid absorbent layer, the hydrophilic fibers are in contact with each other. During absorption of the moisture in the form of body exudates by the absorbent body, even if the superabsorbent polymer particles absorb a moiety of the moisture and swell, a surplus moisture migrates down through the hydrophilic fibers lying among the swollen superabsorbent polymer particles into the second liquid absorbent layer underlying the first liquid absorbent layer and absorbed by this second liquid absorbent layer. In the second liquid absorbent layer, the moisture diffuses through the hydrophilic fibers in the longitudinal direction and in the transverse direction. In the absorbent body having such core material, even when the absorbent body is subjected to a suppress strength in the thickness direction such as own body weight of the wearer, the moiety of moisture once having been absorbed by the superabsorbent polymer particles in the first liquid absorbent layer is not readily separated and discharged therefrom. On the other hand, the moiety of moisture absorbed or retained by the hydrophilic fibers in the second liquid absorbent layer is blocked by the superabsorbent polymer particles having absorbed the moiety of moisture and swollen in the first liquid absorbent layer from migrating upward. Consequently, it is possible for this absorbent body to prevent the moiety of moisture once having been absorbed from flowing back outward from the absorbent body, i.e., to prevent a rewet phenomenon from occurring, thereby alleviating a sense of discomfort the wearer of the absorbent article using this absorbent body might experience.

The method of producing the absorbent body for the absorbent articles according to the second aspect of the present invention facilitates the absorbent body according to the first aspect of the present invention to be easily obtained merely by appropriately regulating the distance dimensions between the dispersing pipes and the support.

BRIEF DESCRIPTION OF DRAWINGS

The drawings illustrate specific embodiments of the present invention including optional and preferred embodiments as well as essential features of the invention.

FIG. 4 is a diagram exemplarily illustrating a diffuser pipe in plan view (a), in lateral view (b) and in end view (c).

DESCRIPTION OF EMBODIMENTS

Embodiments described below relate to a disposable diaper as an example of the absorbent articles using the absorbent body according to the present invention and a method for producing this absorbent body as illustrated in FIGS. 1 to 19, including the both optional and preferred features as well as those features which are essential features of the present invention.

Figure 1:
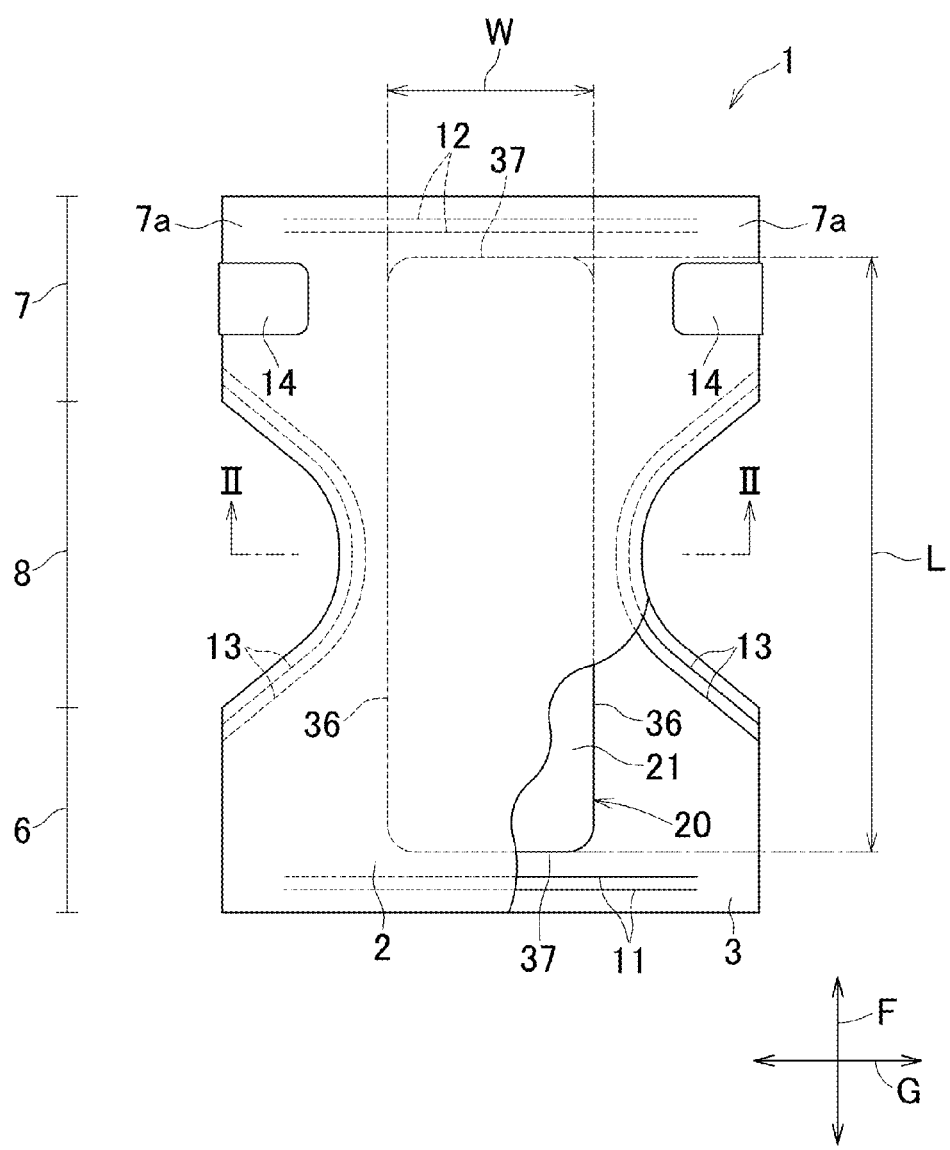
FIG. 1 is a partially cutaway plan view of a disposable diaper as one example of absorbent articles.

A diaper 1 illustrated in FIG. 1 is of open-type using an absorbent body 20 according to the present invention. The diaper 1 includes a liquid-permeable topsheet 2, a liquid-impermeable backsheet 3 and the absorbent body 20 interposed between these two sheets 2, 3. These two sheets 2, 3 extend outward beyond a peripheral edge of the absorbent body 20, overlap with each other outside the peripheral edge and are joined to each other, for example, with of hot melt adhesive (not shown). The diaper 1 has a longitudinal direction, a transverse direction and a thickness direction respectively indicated by double-headed arrows F, G and H (See FIG. 1 together with FIG. 2). In the longitudinal direction F, the diaper 1 is zoned into a front waist region 6, a rear waist region 7 and a crotch region 8 extending between these front and rear waist regions 6, 7. The front waist region 6 and the rear waist region 7 are disposed with a plurality of waist elastics 11, 12 extending in the transverse direction G between the topsheet 2 and the backsheet 3 and contractibly secured under tension between these two sheets 2, 3. The crotch region 8 is disposed with a plurality of leg elastics 13 extending in the generally longitudinal direction F between the topsheet 2 and the backsheet 3 and contractibly secured under tension between these two sheets 2, 3.

Tape fasteners 14 for putting the diaper 1 on the wearer's body are attached to both side edge portions 7a of the rear waist region 7.

Figure 2:
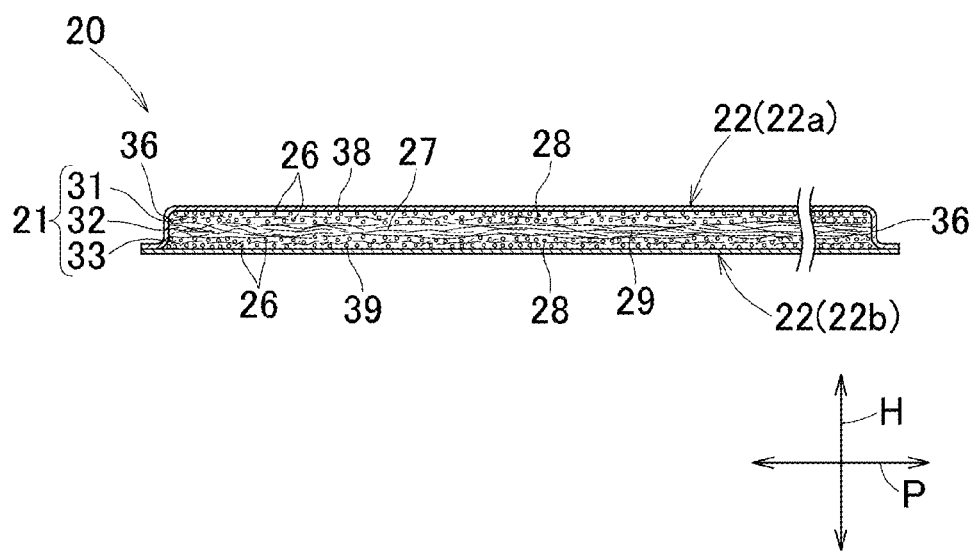
FIG. 2 is a cross-sectional view of an absorbent body.

Referring to FIG. 2, the absorbent body 20 has a core material 21 formed of hydrophilic material and a cover sheet 22 adapted to cover the core material 21. The core material 21 has a mass per unit area of 650 g/m$^2$ or less and contains superabsorbent polymer particles 26 ranging 150 to 350 g/m$^2$ having liquid absorption capacity of 10 or more times of own mass and hydrophilic fibers 27 ranging of 150 to 400 g/m$^2$. The core material 21 includes a first layer 31 and a third layer 33 formed of a first liquid absorbent layer 28 in which the superabsorbent polymer particles 26 and the hydrophilic fibers 27 such as comminuted wood pulp (i.e., fluff pulp) are mixed together and a second layer 32 formed of a second liquid absorbent layer 29 containing the hydrophilic fibers but absolutely or substantially not containing the superabsorbent polymer particles 26. These first, second and third layers 31, 32, 33 are layered in the thickness direction H in descending order. The first liquid absorbent layer 28 contains the superabsorbent polymer particles 26 at least of 50 g/m$^2$ and a quantity of the hydrophilic fibers 27 sufficient to limit a volume fraction (as described later) in a range of 2.4 to 7%. The second liquid absorbent layer 29 has the hydrophilic fibers 27 at least of 70 g/m$^2$. Between the first liquid absorbent layer 28 and the second liquid absorbent layer 29, for example, between the first layer 31 and the second layer 32, the hydrophilic fibers 27 contained in the respective layers 31, 32 are in contact with each other. The core material 21 has first edge portions 36 extending along respective side edges thereof in the transverse direction G, second edge portions 37 (See FIG. 1) extending along respective ends thereof in the longitudinal direction F, and a top portion 38 and a bottom portion 39 in the thickness direction H. In the core material 21 exemplarily illustrated, the first, second and third layers 31, 32, 33 respectively extend to the first edge portions 36 and the second edge portions 37. In the preferred core material 21, the first liquid absorbent layer 28 and the second liquid absorbent layer 29 extend at least to the one pair of the pair of first edge portions 36 and the pair of the second edge portions 37 and are capable of absorbing body exudates along this pair of edge portions as well. The top portion 38 of the core material 21 faces a wearer's skin (not shown) and the bottom portion 39 faces the wearer's garment (not shown).

Referring further to FIG. 2, the cover sheet 22 is formed from an upper cover sheet 22a adapted to cover the first edge portions 36 and the top portion 38 of the core material 21 and a lower cover sheet 22b adapted to wrap the bottom portion 39. The upper cover sheet 22a and the lower cover sheet 22b extend outward beyond the periphery of the core material 21, overlap with each other outside the periphery of the core material 21 and are joined to each other preferably with hot melt adhesive. In this regard, both the upper cover sheet 22a and the lower cover sheet 22b may be optionally joined at intervals to the surface of the core material 21 with hot melt adhesive or not joined to the surface of the core material 21. The upper cover sheet 22a is liquid-permeable and may be formed of nonwoven fabrics, for example, SMS nonwoven fabrics (spun bonded/melt blown/spun bonded nonwoven fabrics) having a mass per unit area in a range of 8 to 15 g/m$^2$, tissue paper, perforated plastic films having a thickness in a range of 0.01 to 0.05 mm or the like. The lower cover sheet 22b may be liquid-permeable or liquid-impermeable and formed of the liquid-permeable nonwoven fabrics or tissue paper being the same as them used for the upper cover sheet 22a, liquid-impermeable plastic films having a thickness in a range of 0.01 to 0.03 mm or the like.

In the core material 21, as material for the superabsorbent polymer particles 26, polymers widely used in the relevant technical field such as polyacrylate-based polymers or starch-based polymers may be used. In the core material 21, it is also possible to use two different types of the superabsorbent polymer particles 26 for the first layer 31 and the third layer 33, respectively. For example, the superabsorbent polymer particles 26 having a relatively low body exudates absorption rate may be used for the first layer 31 and the superabsorbent polymer particles 26 having a relatively high body exudates absorption rate may be used for the third layer 33. It is also possible to use the superabsorbent polymer particles 26 having a relatively large particle diameter for the first layer 31 and to use the superabsorbent polymer particles 26 having a relatively small particle diameter for the third layer 33. As material for the hydrophilic fibers 27, liquid-absorbent natural fibers such as fluff pulp or moisture-absorbent regenerated fibers such as rayon fibers or cuprammonium fibers may be used. The hydrophilic fibers 27 are preferably short fibers each having a length in straightened state of 20 mm or less. As used herein the terms "hydrophilic fibers" means fibers produced from materials having a hydroxyl group in its molecular structure.

Various modifications may be added to the exemplarily illustrated core material 21. For example, it is possible to compose the first layer 31 and the third layer 33 of the core material 21 of the second liquid absorbent layer 29 containing the hydrophilic fibers 27 but not containing the superabsorbent polymer particles 26 and to compose the second layer 32 of the first liquid absorbent layer 28 containing both the superabsorbent polymer particles 26 and the hydrophilic fibers 27. Here, it is also possible to use the hydrophilic fibers having different behaviors depending on whether the hydrophilic fibers are used for the first layer 31 or the third layer 33. For example, the fluff pulp may be used for the first layer 31 and the rayon fibers may be used for the third layer 33. The core material 21 is not limited to the three-layer construction as in the exemplarily illustrated embodiment but may be of four or more layer construction. The core material 21 having four or more layers also is formed in the manner that the first liquid absorbent layer 28 in which the superabsorbent polymer particles 26 and the hydrophilic fibers 27 are mixed with each other and the second liquid absorbent layer 29 containing the hydrophilic fibers 27 but not containing the superabsorbent polymer particles 26 may be alternately lapped over. Here, the first layer 31 may be formed of the first liquid absorbent layer 28 or the second liquid absorbent layer 29. In this regard, if it is desired to minimize a 'rewet quantity' as described later, the third layer 33 is formed preferably of the first liquid absorbent layer 28. In other words, the absorbent body 20 preferably has the first liquid absorbent layer 28 at least one of the top portion 38 and the bottom portion 39.

In the core material 21 having the structure formed of at least three layers, the hydrophilic fibers 27 contained in the respective layers 31, 32 are in contact with one another between the first liquid absorbent layer 28 and the second liquid absorbent layer 29, for example, between the first layer 31 and the second layer 32 and, in consequence, moisture in the first layer 31 is migratable through the hydrophilic fibers 27 to the second layer 32. As used here, the term "the hydrophilic fibers 27 are in contact with one another between the first and second liquid absorbent layers 28, 29' includes a case in which the hydrophilic fibers 27 are present so as to stride the first and second liquid absorbent layers 28, 29. In the second layer 32, moisture extensively diffuses in the longitudinal direction and in the transverse direction G through the hydrophilic fibers 27 so that the liquid absorption capacity of the second layer 32 may be fully utilized. When the superabsorbent polymer particles 26 aqueous liquid, swell and form gelled blocks in the first layer 31, the gelled blocks restrict the flow of from moisture the second layer 32 toward the first layer 31, i.e., a rewet phenomenon, thereby creating a discomfort wet feeling against the wearer after urination. Even if urination occurs again after the superabsorbent polymer particles 26 have swollen, the hydrophilic fibers 27 in the first layer 31 facilitate the quantity of urine newly discharged to flow through the first layer 31, to be absorbed by the second layer 32 and to be retained therein. The core material 21 and the absorbent body 20 containing this core material 21 functioning in this manner are sufficiently useful overall for the absorbent articles to be used, not only for the diaper having the configuration as exemplarily illustrated, but also for the other various kinds of absorbent articles having different configurations such as diapers for incontinent patients, urine-absorbent pad and sanitary napkin.

Figure 3:
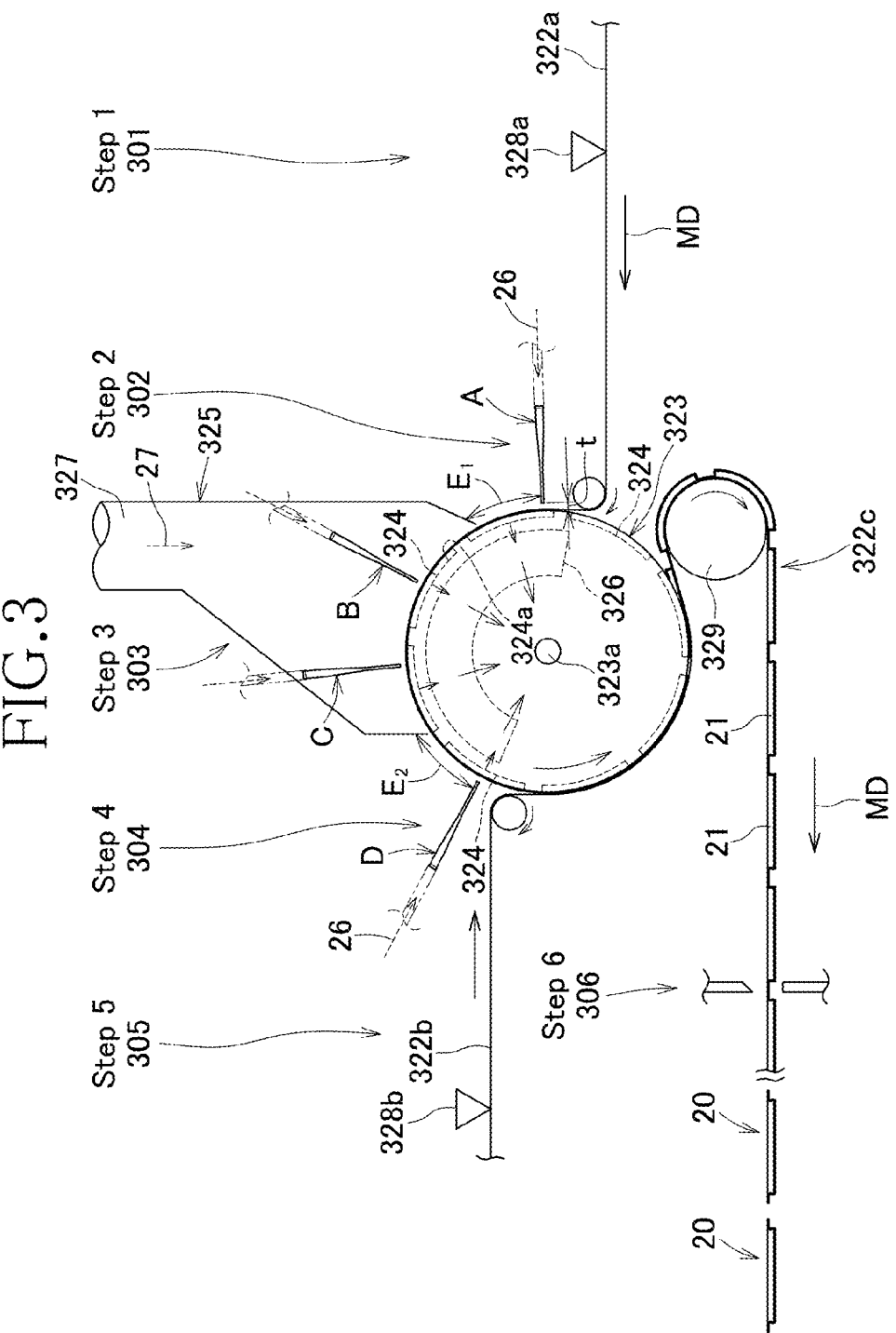
FIG. 3 is a schematic diagram illustrating a process flow for production of the absorbent body.

FIG. 3 is a schematic diagram illustrates a production process including a first to sixth steps 301, 306 for the absorbent body 20 exemplarily illustrated in FIG. 2 and the other embodiments of the absorbent body according to the present invention.

In the first step 301, a first web 322a which is a continuum of the upper cover sheet 22a is continuously fed in a machine direction MD by supports such a conveying rollers and endless belt (not shown) and, in course of being fed, coated by an adhesive coater 328a with hot melt adhesive (not shown). The first web 322a is continuously coated with hot melt adhesive in the machine direction MD and/or in a cross direction CD.

In the second step 302, a rotary drum 323 adapted for formation of the core material 21 rotates in a counterclockwise direction as viewed in FIG. 3 and the first web 322a running in the machine direction MD is loaded on a peripheral surface of the rotary drum 323. On the peripheral surface of the rotary drum 323, a plurality of cavities 324 each having a shape corresponding to one of the core material 21 is arranged at regular intervals in a peripheral direction. A dimension of the cavity 324 in the peripheral direction of the rotary drum 323 is approximately the same as a length L (See FIG. 1) of the core material 21, a dimension of the cavity 324 in parallel to a rotary shaft 323a of the rotary drum 323 is approximately the same as a width W (See FIG. 1) of the core material 21 and a depth of the cavity 324 is approximately the same as the thickness of the core material 21. The rotary drum 323 cooperates with a suction means 326 situated within the rotary drum 323. The suction means 326 connected with a vacuum suction conduit (not shown) and functions so that, when the cavities 324 successively come just above the suction means 326 as the rotary drum rotates, the cavitis 324 may be subjected to a vacuum suction effect. Such rotary drum 323 is a part of the support for the core material 21, the first web 322a and the other materials to convey the materials in the machine direction MD.

Also in the second step 302, a first dispersing pipe A extending in a direction crossing with the rotary shaft 323a of the rotary drum 323 is set toward the peripheral surface of the rotary drum 323. When the cavity 324 is subjected to the vacuum suction effect during rotation of the rotary drum 323, the first web 322a is deformed so as to conform the configuration of the cavity 324. Then the cavity 324 comes to a position facing the first dispersing pipe A and at the same time the superabsorbent polymer particles 26 are dispersed from the first dispersing pipe A toward the cavity 324 so that the superabsorbent polymer particles 26 in the first layer 31 may be deposited on the upper cover sheet 22a of the core material 21 on a bottom portion 324a of the cavity 324. A distance t between the bottom portion 324a of the cavity 324 and a tip of the first dispersing pipe A is preferably in a range of 5 to 100 mm. As used herein, the term "distance dimension between the support and the dispersing pipe" means the distance t between the tip of the dispersing pipe and the bottom portion 324a of the cavity 324.

In the third step 303, the cavity 324 having left the second step 302 is guided into a chamber 325 formed above the rotary drum 323. The chamber 325 partially covers the peripheral surface of the rotary drum 323 in a circumferential direction of the rotary drum 323. A top portion of the chamber 325 is connected to an air-conveying conduit 327 for the hydrophilic fibers 27 and the cavity is subjected to a vacuum suction effect by the suction means 326. The hydrophilic fibers 27 fed via the conduit 327 are dispersed under the vacuum suction effect of the suction means onto the cavity 324 guided into the chamber 325 to form portions respectively corresponding to the hydrophilic fibers 27 in the first layer 31 and the second layer 32 of the core material 21.

Within the chamber 325, a second dispersing pipe B and a third dispersing pipe C serving to dispersed the superabsorbent polymer particles 26, thereby forming the first liquid absorbent layer 28 containing the superabsorbent polymer particles 26 and the hydrophilic fibers 27 like for the first layer 31 are arranged along the peripheral surface of the rotary drum 323. While these second and third dispersing pipes B, C are not adapted to be used to form the core material 21 having the structure illustrated in FIG. 2, the distance t between the bottom portion 324a of the cavity 324 and the tips of the second and third dispersing pipes B, C is preferably in a range of 5 to 20 mm in a particular production process of the core material 21 for which these dispersing pipes B, C are used. When this distance t is larger than 20 mm within the chamber 325, the superabsorbent polymer particles 26 and the hydrophilic fibers 27 will be readily mixed with one another and it will be difficult to form the second liquid absorbent layer 29 absolutely or substantially containing none of the superabsorbent polymer particles 26. An average flow velocity of discharged air from respective openings 341 of these second and third dispersing pipes B, C is preferably 100 m/sec or less. If the average flow velocity exceeds this value, there will be a higher possibility that the superabsorbent polymer particles 26 might bounce back from the bottom portion 324a and the hydrophilic fibers 27 deposited on the bottom portion 324a of the cavity 324 and fly in all directions in and out the cavity 324.

In the fourth step 304, the superabsorbent polymer particles 26 are dispersed from a fourth dispersing pipe D into the cavity 324 having left the chamber 325 and thereby a portion corresponding to the third layer of the core material 21. Also in the fourth step 304, the cavity 324 is subjected to the vacuum suction effect of the suction means 326.

In the fifth step 305, a second web 322b which is a continuum of the lower cover sheet 22b is coated by an adhesive coater 328b with hot melt adhesive (not shown) at regular intervals in the machine direction MD and/or in the cross direction CD and then continuously fed onto the peripheral surface of the rotary drum 323. Outside the peripheries of the respective cavities 324, the second web 322b overlaps with the first web 322a so as to sandwich the superabsorbent polymer particles 26 and the hydrophilic fibers 27 within the respective cavities 324 and then this assembly is conveyed toward a guide roller 329.

In the sixth step 306, the first web 322a, the superabsorbent polymer particles 26 and the hydrophilic fibers 27 having been set within the cavity 324 now bulge outward from the cavity 324 and, in this way, a third web 322c including the first web 322a, the second web 322b, the superabsorbent polymer particles 26 and the hydrophilic fibers 27 is formed. In the third web 322c, the superabsorbent polymer particles 26 and the hydrophilic fibers 27 form the core material 21 exemplarily illustrated in FIG. 2. Also in the sixth step 306, the third web 322 may be cut between each pair of the adjacent core materials 21, 21 to obtain the individual absorbent bodies 20.

Figure 19:
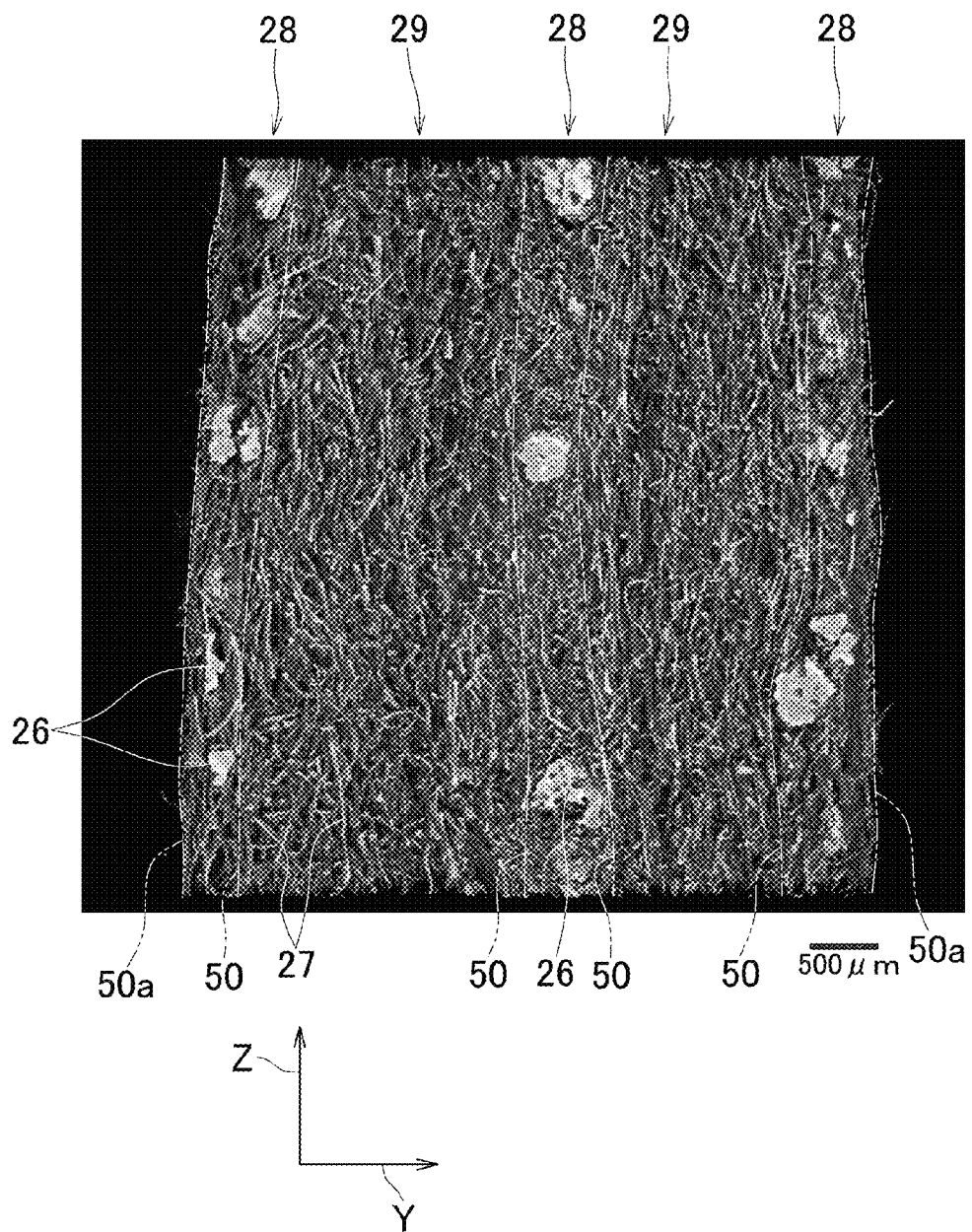
FIG. 19 is an X-ray CT photo showing a stereo image of Y-Z cross-sectional surface of the test piece shown in FIG. 17.

In the production process designed as schematically illustrated in FIG. 3, the hydrophilic fibers 27 may be dispersed within the chamber 325 and the superabsorbent polymer particles 26 may be dispersed from at least one of the first and fourth dispersing pipes A, D located upstream and downstream of the chamber 325, respectively, outside the chamber 325 or the superabsorbent polymer particles 26 may be dispersed from at least one of the second and third dispersing pipes B, C located so as to come close to the cavity 324 within the chamber 325 to obtain, within each of the cavities 324, the first liquid absorbent layer 28 in which the superabsorbent polymer particles 26 and the hydrophilic fibers 27 are deposited so as to be mixed together, thereby forming a layer and the second liquid absorbent layer 29 containing the hydrophilic fibers 27 but none of the superabsorbent polymer particles 26. As illustrated in FIG. 19 described later, the hydrophilic fibers 27 are present between the superabsorbent polymer particles 26 in the first liquid-absorbent layer 28. These hydrophilic fibers 27 are considered to be part of the hydrophilic fibers 27 having been dispersed to form the second liquid absorbent layer 29 after the superabsorbent polymer particles 26 had been dispersed and then have moved between the superabsorbent polymer particles 26. For the first liquid absorbent layer 28 formed in this manner, there is no specific regularity for distribution of the superabsorbent polymer particles 26 and the hydrophilic fibers 27. In other words, the first liquid absorbent layer 28 may be defined as the layer in which the superabsorbent polymer particles 26 and the hydrophilic fibers 27 are mixed with one another. On the other hand, in the second liquid absorbent layer 29 formed of the hydrophilic fibers 27, none of the superabsorbent polymer particles 26 is present. In this regard, there is a possibility that a minute quantity or a substantially nil quantity of the superabsorbent polymer particles 26 may be present in the second liquid absorbent layer 29, for example, due to causes above an actual ability to manage the production process.

Referring to FIG. 3, the first to fourth dispersing pipes A, B, C, D may be selectively used so as to correspond to the desired cross-sectional configuration of the core material 21 and, for example, the first and fourth dispersing pipes A, D may be used to obtain the core material 21 illustrated in FIG. 2. It is possible for the first to fourth dispersing pipes A, B, C, D to change a quantity of the superabsorbent polymer particles 26 discharged per unit time.

Referring also to FIG. 3, the cavities 324 formed on the peripheral surface of the rotary drum 323 may be arranged so that the cavity may be continuous around the entire circumference of the rotary drum 323 or the respective cavities may be arranged at regular intervals around the entire circumference of the rotary drum 323. The superabsorbent polymer particles 26 and/or the hydrophilic fibers 27 dispersed within the chamber 325 might collide against the peripheral surface of the rotary drum 323, scatter within the chamber 325 and make it difficult to form the core material 21 containing the first liquid absorbent layer 28 and the second liquid absorbent layer 29 which are distinguishable from each other. In view of this, the peripheral surface of the drum may be formed preferably with a continuous cavity 324 over the entire circumferential range and the area of the exposed peripheral surface of the rotary drum 323 may be dimensioned as small as possible within the chamber 325 to resolve the problem as described above. The continuous core material obtained with use of the continuous cavities 324 may be successively cut in a predetermined dimension in the machine direction MD after the continuous cavities 324 have left the chamber 325 to obtain the individual core materials 21. The continuous cavities or the individual cavities 21 may be covered with appropriate cover sheets such as the first and second cover sheets 322a, 322b in an appropriate step not illustrated.

For the cavities 324 formed on the peripheral surface of the rotary drum 323 at regular intervals, the spacing dimension between a pair of the cavities 324 adjacent in the circumferential direction is preferably minimized, for example, to a range of 5 to 10 mm to restrict a possibility that the superabsorbent polymer particles 26 and/or the hydrophilic fibers might scatter. Here, it is also preferable to set a distance E1 in the circumferential direction of the rotary drum 323 between the first dispersing pipe A and the chamber 325 and a distance E2 in the same direction between the fourth dispersing pipe D and the chamber 325 so that both the distance E1 and the distance E2 are not smaller than a dimension of the cavity 324 as measured in the circumferential direction of the rotary drum 323.

FIG. 4 illustrates, in (a), (b) and (c) thereof, a figuration of the first to fourth dispersing pipes A, B, C, D exemplarily illustrated in FIG. 3. The first to fourth dispersing pipes A, B, C, D exemplarily illustrated are preferably the same in shape as well as in size and a dispersed opening 341 formed at respective lower ends of FIG. 4 (a) illustrating a front geometry and FIG. 4 (b) illustrating a side geometry has a dimension M and a dimension N as indicated in FIG. 4 (c). The dimension M is the dimension in the machine direction MD and in a range of 30±5 mm in a preferable example of the first to fourth dispersing pipes A, B, C, D. The dimension N is the dimension in the cross direction CD orthogonal to the machine direction MD and set to be the same as the width W (See FIG. 1) of the core material 21 or larger than the width W. A top end 342 of the first to fourth dispersing pipes A, B, C, D is connected to a conduit 343 serving to air-convey the superabsorbent polymer particles 26.

As will be described in detail hereunder, concerning the configuration and the performance of the core material in which a mass per unit area of the superabsorbent polymer particles is about 250 g/m$^2$, amass per unit area of the hydrophilic fibers is about 200 g/m$^2$ and a total mass is 450 g/m$^2$, the inventors compared the embodiments in which the superabsorbent polymer particles 26 are distributed in layered state with the comparative examples in which the superabsorbent polymer particles 26 and the hydrophilic fibers 27 are in a mixed state in entirety of the core material.

Configuration of Core Material, Observation and Evaluation of Performance Thereof (1)

Using the production process illustrated in FIG. 3, the absorbent body 20 having a size defined by L=200 mm and W=100 mm and the configuration illustrated in FIG. 1 was produced. The dimension L is the dimension in the machine direction MD and the dimension W is the dimension in the cross direction CD. The respective directions MD and CD respectively correspond to the longitudinal direction F and the transverse direction G. A spacing dimension between a pair of the cavities 324 adjacent in the circumferential direction on the rotary drum 323 was set to 10 mm. As the hydrophilic fibers 27 contained in the core material 21, comminuted wood pulp (fluff) obtained by processing PULP NB416 manufactured by Weyehaeuser Co., Ltd. was used. As the superabsorbent polymer particles 26, Superabsorbent polymer UG860D manufactured by Sumitomo Seika Chemicals Co., Ltd. was used. As the first web 322a and the second web 322b, hydrophilized spun bonded/melt blown/spun bonded nonwoven fabrics having a mass per unit area of 10 g/m² (manufactured by CNC International Co., Ltd.) was used. Items for observation and evaluation of the absorbent body and respective results are described hereunder.

1. Mass of Core Material (1) The absorbent body was cut in a size of 50 mm×50 mm to obtain test pieces.

(2) Each of the test pieces was weighed with use of an electronic scale and an average value of mass was calculated from respective values of ten test pieces.

(3) Respective basis weight (mass per unit area) of the upper cover sheet and the lower cover sheet and a basis weight (mass per unit area) of hot melt adhesive used for these cover sheets were obtained.

(4) Mass per 1 m² of the core material was obtained on the basis of a formula as follows:

Mass of core material (g/m²)=(average value of absorbent body's mass)/(0.05×0.05)−(mass per 1 m² of upper cover sheet and lower cover sheet)−(mass per 1 m² of hot melt adhesive used for upper cover sheet) and lower cover sheet)   (formula 1)

2. Thickness of Absorbent Body and Core Material (1) The absorbent body was cut in a size of 50 mm×50 mm to obtain test pieces.

(2) Thickness of the respective test pieces was measured with use of DIAL THICKNESS GAUGE J-B type manufactured by OZAKI MFG CO., LTD (Peacock) including a gauge head having a diameter of 50 mm and an average value calculated from values measured on ten test pieces was adopted as the thickness of the absorbent body. Five sheet pieces each having a size of 50 mm×50 mm were cut out from the first and second webs 322a, 322b illustrated in FIG. 3, respectively, and a gauge head having a diameter of 50 mm was used with DIAL THICKNESS GAUGE J-B type to obtain average thickness values from respective groups of five sheet pieces. The respective average values were adopted as thickness of the upper cover sheet and the lower cover sheet.

3. Cross-Section Observation of Core Material (1) Compound liquid of 99.5 mass % of distilled water and 0.5 mass % of edible dye Blue No. 1 (manufactured by KOYO PRODUCT Co. Ltd.) was prepared as coloration testing liquid.

(2) The absorbent body was cut in a size of 100 mm×50 mm to obtain test pieces each having a cross-section surface for observation.

(3) Mass of the test piece was measured with use of electronic scale.

(4) Each test piece was put in a container having a volume slightly larger than the test piece and filled with coloration testing liquid having mass 30 times that of the test piece so that the liquid may be absorbed by the test piece. The test piece immersed in the liquid was left as it is for 2 minutes.

(5) The superabsorbent polymer particles and the hydrophilic fibers tumbled from the cross-sectional surface of the test piece were removed with use of a pair of tweezers to facilitate the cross-section observation.

(6) The cross-section was visually observed to judge whether the first liquid absorbent layer 28 and the second liquid-absorbent layer 29 according to the present invention are present or not.

4. Wicking Distance at an Angle of 45°

Figure 5:
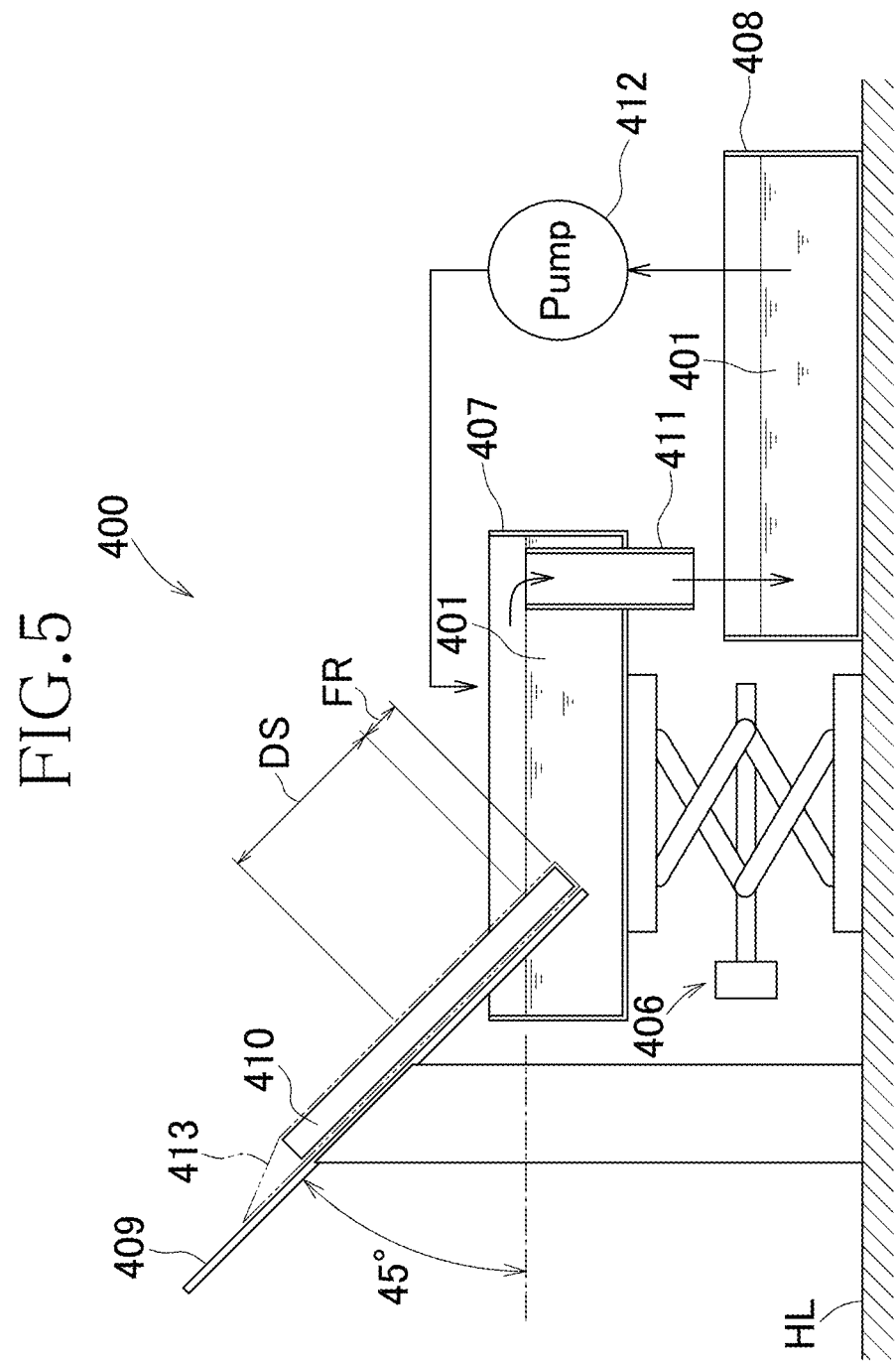
FIG. 5 is a side view of a wicking tester.
Figure 6:
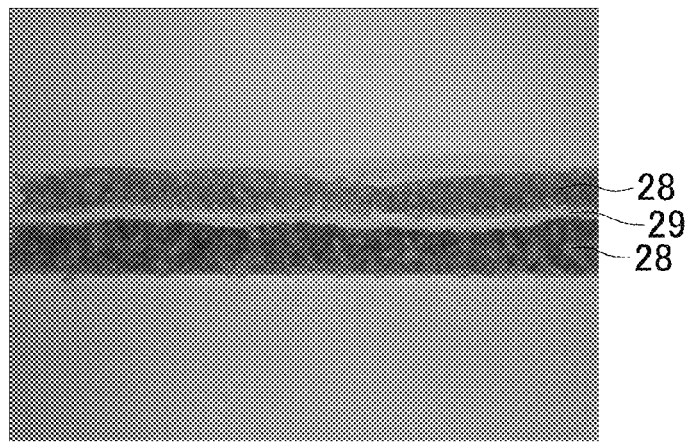
FIG. 6 is a photo showing cross-sectional observation of the absorbent body according to an embodiment 1.
Figure 7:
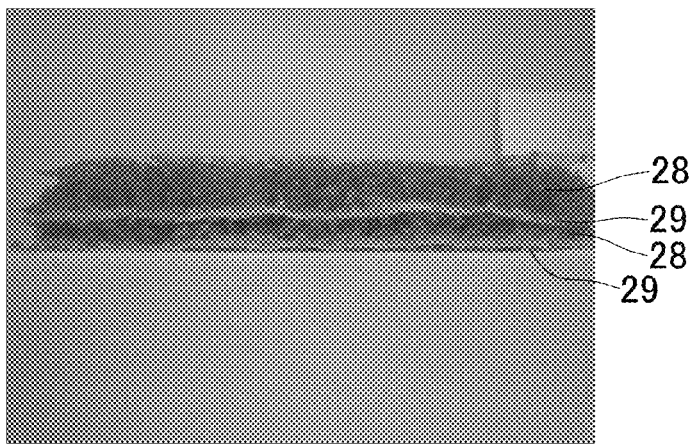
FIG. 7 is a photo showing cross-sectional observation of the absorbent body according to an embodiment 2.
Figure 8:
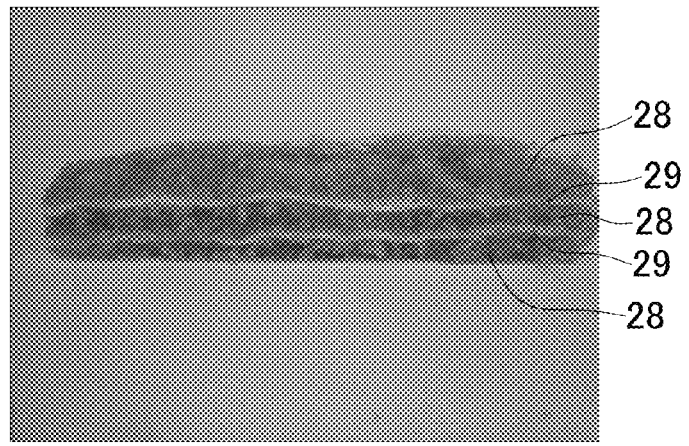
FIG. 8 is a photo showing cross-sectional observation of the absorbent body according to an embodiment 3.
Figure 9:
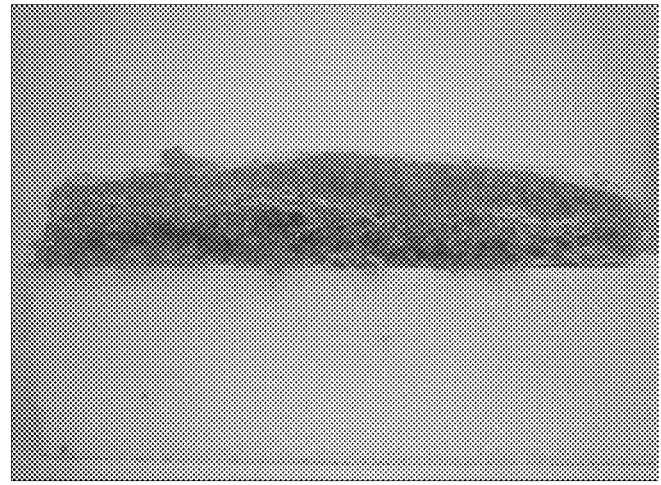
FIG. 9 is a photo showing cross-sectional observation of the absorbent body according to a comparative example 1.
Figure 10:
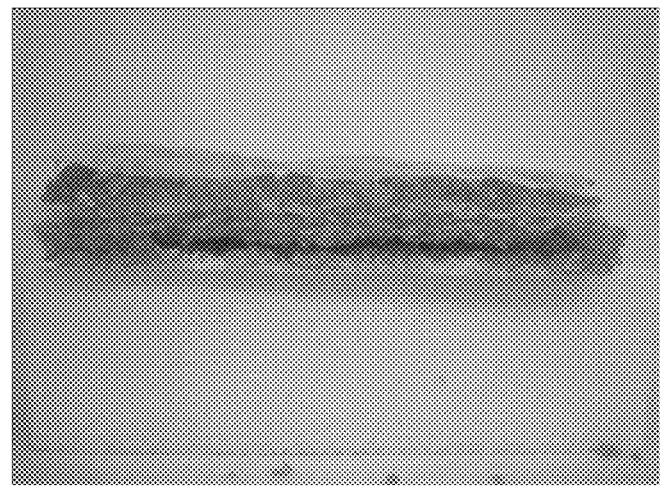
FIG. 10 is a photo showing cross-sectional observation of the absorbent body according to a comparative example 2.

(1) A wicking distance in the absorbent body was measured with use of a testing equipment 400 illustrated in FIG. 5. On this testing equipment 400, test pieces 410 (See FIG. 5) cut out from the absorbent body each having a dimension L in the machine direction MD of 100 mm and a dimension W in the cross direction CD of 50 mm were used. The machine direction MD corresponds to the longitudinal direction F of the absorbent body and the cross direction CD corresponds to the transverse direction G of the absorbent body.

(2) The testing equipment specifically includes various parts as the following: a lifting and lowering device 406 placed on a horizontal plane HL, a first water tank 407 loaded on the lifting and lowering device 406, a second water tank 408 placed on the horizontal plane HL and a tilted plate 409 tilted at an angle of 45° with respect to the horizontal plane HL. The first water tank 407 is filled with colored physiological saline 401. A drain pipe 411 extends from the first water tank 407 to the second water tank 408 so that a surplus of the colored physiological saline 401 in the first water tank 407 may run down into the second water tank 408. There is a circulation pump 412 between the first water tank 407 and the second water tank 408 and adapted to reflux the colored physiological saline 401 from the second water tank 408 to the first water tank 407 continuously or at regular time intervals so that the liquid level of the colored physiological saline 401 may remain constant. The liquid level relative to the horizontal plane HL may be adjusted by the lifting and lowering device 406. The tilted plate 409 includes a fixture (not shown) by means of which the test piece 410 which is uncovered or contained in a water-permeable bag 413 is fixed to the tilted plate 409. Test piece 410 was fixed on the tilted plate 409 in a manner that the upper cover sheet may face upward, the machine direction MD may correspond to a vertical direction of the tilted plate 409 and a lower end of the test piece 410 may align with a lower end of the tilted plate 409.

(3) In measurement of wicking distance, after the test piece 410 had been fixed to the tilted plate 409, the lifting and lowering device 406 was operated to immerse a lower end portion FR of the test piece 410 only by a length of 10 mm into the colored physiological saline 401 to start the wicking test. 2 minutes after immersion, the lifting and lowering device 406 was operated again to lower the first water tank 407 was lowered until the entirety of the lower end portion FR was exposed. Through the upper cover sheet, the maximum arrival distance DS of the colored physiological saline from the lower end portion FR of the test piece 410 was measured with use of a straight ruler. An average value of the maximum arrival distance calculated from measured values obtained on five test pieces was adopted as "wicking distance at an angle of 45°".

(4) Measurement of "wicking distance at an angle of 45°" was conducted in the specific steps as follow:

a. First physiological saline was prepared (compound liquid of 99.1 mass % of distilled water and 0.9 mass % of sodium chloride).

b. 0.5 mass % of Edible dye Blue No. 1 manufactured by Koyo Produck Co. Ltd. was dissolved in 99.5 mass % of the first physiological saline to prepare the colored physiological saline 401.

c. Mass of respective five test pieces 410 (L=100 mm, W=50 mm) was weighed with use of the electronic scale.

d. Each test piece was put in a container having a volume slightly larger than the test piece and filled with the first physiological saline having mass 10 times that of the test piece so that the first physiological saline may be absorbed by the test piece under no agitation.

e. 5 minutes after the start of absorption, the test piece 410 was placed on the tilted plate 409 of the testing equipment 400 illustrated in FIG. 5 and the lifting and lowering device 406 was lifted until the lower end portion FR of the test piece 410 is immersed in the colored physiological saline 401 only by a length of 10 mm as observed through the upper cover sheet and was left as it is for 1 minute.

f. 1 minute after having been left as it is, the lifting and lowering device 406 was lowered and the maximum arrival distance DS of the core material defined from the lower end portion FR of the test piece 410 to the portion colored by the colored physiological saline 401 was measured with use of the straight ruler. In other words, when the arrival distance of the colored physiological saline 401 in the transverse direction of the test piece 410 has changed, the maximum arrival distance of the colored physiological saline was measured.

g. An average value of the maximum arrival distance calculated from measured values obtained on five test pieces was adopted as "wicking distance at an angle of 45°".

(note 1) Considering a possibility that the hydrophilic fibers and/or the superabsorbent polymer particles might fall off from the test piece 410, the test piece 410 was covered with open net or the like to conduct the test without anxiety that the test piece 410 might crumble.

(note 2) As the open net, Nylon Mesh N-NO250HD manufactured by NBC Meshtec Inc. was used.

(note 3) In the step d of "wicking test at an angle of 45°", the test piece was immersed in the first physiological saline so that the test piece may absorb this first physiological saline on the assumption of the case in which urination may occur on the diaper put on the wearer's body already in a wet condition.

(note 4) The test piece 410 was tilted at an angle of 45° on the assumption that the absorbent body of the diaper put on the wearer's body is in a state of rising slope from the crotch region toward the waist regions and urine is discharged onto this crotch region.

(note 5) If "the wicking distance at an angle of 45°" is relatively large, it will be meant that the quantity of urine discharged onto the crotch region rapidly diffuses into the front and rear waist regions without anxiety that a significant quantity of urine might remain in the crotch region and, in consequence, sense of wetness experienced by the wearer in the crotch region is alleviated.

Embodiment 1

In the production process illustrated in FIG. 3, comminuted PULP NB416 as the hydrophilic fibers was air-conveyed into the chamber 325 and dispersed toward the cavity 324 within the chamber 325. The superabsorbent polymer particles 26 were volumetrically fed through a screw feeder and then these superabsorbent polymer particles 26 were air-conveyed to the first and fourth dispersing pipes A, D through which nearly equal quantity of the superabsorbent polymer particles 26 per unit time was dispersed toward the interior space of the cavity 324. Respective quantities fed per unit time of the hydrophilic fibers 27 and the superabsorbent polymer particles 26 were controlled so that the hydrophilic fibers 27 may contain about 45 mass % and the superabsorbent polymer particles 26 may contain about 55 mass % in the core material 21 obtained and a circumferential velocity of the rotary drum 323 so that the core material 21 may have a mass per unit area of 450 g/m$^2$. In consequence, the core material 21 containing the hydrophilic fibers 27 having a mass per unit area of about 200 g/m$^2$ and the superabsorbent polymer particles having a mass per unit area of about 250 g/m$^2$ was obtained. As material for the first web 322a which is the continuum of the upper cover sheet 22a and the second web 322b which is the continuum of the lower cover sheet 22b, breathable and liquid-permeable spun bonded/melt blown/spun bonded nonwoven fabrics having a mass per unit area of 10 g/m$^2$ was used. As the first and fourth dispersing pipes A, D, those in which the opening 341 has the dimension M of 30 mm and the dimension N of 115 mm were used (See FIG. 4). The first and fourth dispersing pipes A, D were set so that a distance t may be maintained between from the respective openings 341 to the bottom surface of the cavity 324. A flow velocity of discharged air at the openings 341 was set to 46 m/sec. Evaluation result for the absorbent body 20 obtained in the manner as has been described above was listed in TABLE 1. Result of the observation for the absorbent body 20 including the cross-section of the core material 21 was as seen from the photo in FIG. 6. The core material 21 in the absorbent body 20 was of three-layered structure in which the second liquid absorbent layer 29 formed of only the hydrophilic fibers 27 was sandwiched between a pair of the first liquid absorbent layers 28 each containing the superabsorbent polymer particles 26 and the hydrophilic fibers 27 in mixed state. The hydrophilic fibers 27 being present in the first liquid absorbent layer 28 were a part of the hydrophilic fibers 27 used to obtain the second liquid absorbent layer having migrated into gaps between the superabsorbent polymer particles 26.

Embodiment 2

The absorbent body of four-layered structure according to the embodiment 2 was obtained by using the arrangement similar to that in the embodiment 1 except that the second and fourth dispersing pipes B, D was used to spread the superabsorbent polymer particles 26, the distance t for the second dispersing pipe B was set to 10 mm and the flow velocity of discharged air at the opening 341 of the second dispersing pipe B was set to 46 m/sec. Evaluation result for the absorbent body 20 obtained in the manner as has been described above was listed in TABLE 1. Result of the observation for the absorbent body 20 including the cross-section of the core material 21 was as seen from the photo in FIG. 7 and the core material 21 had four-layered structure including the first liquid absorbent layer 28 and the second liquid absorbent layer 29 alternately overlapping with each other. The hydrophilic fibers 27 being present in the first liquid absorbent layer 28 were a part of the hydrophilic fibers 27 used to obtain the second liquid absorbent layer 29 having migrated between the superabsorbent polymer particles 26.

Embodiment 3

The absorbent body 20 of five-layered structure according to the embodiment 3 was obtained by using the arrangement similar to that in the embodiment 2 except that the first, second and fourth dispersing pipes A, B, D were used, the distance t was set to 20 mm for the first and fourth dispersing pipes A, D and set to 10 mm for the second dispersing pipe B. Evaluation result for the absorbent body 20 obtained in the manner as has been described above was listed in TABLE 1, the result of the observation for the absorbent body 20 including the cross-section of the core material 21 was as seen from the photo in FIG. 8 and the core material 21 had five-layered structure including the first liquid absorbent layer 28 and the second liquid absorbent layer 29 alternately overlapping with each other. The hydrophilic fibers 27 being present in the first liquid absorbent layer 28 were a part of the hydrophilic fibers 27 used to obtain the second liquid absorbent layer 29 having migrated between the superabsorbent polymer particles 26.

Embodiment 4

The absorbent body 20 according to the embodiment 4 was obtained by using the arrangement similar to that in the embodiment 1 except that only the second dispersing pipe B illustrated in FIG. 3 to spread the superabsorbent polymer particles 26 and the distance t for the second dispersing pipe B was set to 15 mm. Evaluation result for the absorbent body 20 obtained in the manner as has been described above was listed in TABLE 1. Based on the cross-section observation of the absorbent body 20, it was found that the cross-section of the core material 21 has a three-layered structure in which the first liquid absorbent layer 28 is interposed between a pair of the second liquid absorbent layers 29.

Embodiment 5

The absorbent body 20 according to the embodiment 5 was obtained by using the arrangement similar to that in the embodiment 4 except that the distance t for the second dispersing pipe B in the embodiment 4 was set to 20 mm. Evaluation result for the absorbent body 20 obtained in the manner as has been described above was listed in TABLE 1. Based on the cross-section observation of the absorbent body 20, it was found that the cross-section of the core material 21 has a three-layered structure in which the first liquid absorbent layer 28 is sandwiched between a pair of the second liquid absorbent layers 29.

Embodiment 6

To spread the superabsorbent polymer particles 26, the second and third dispersing pipes B, C illustrated in FIG. 3, of which the openings 341 have the dimension M set to 15 mm, respectively. The distance t for these second and third dispersing pipes B, C was set to 10 mm and the average flow velocity of discharged air at the openings 341 were set to 92.3 m/sec. used. In the other aspects, the arrangement similar to that in the embodiment 1 was used to obtain the absorbent body 20 according to the embodiment 6. Evaluation result for the absorbent body 20 was listed in TABLE 1. Based on the cross-section observation of the absorbent body 20, it was found that the core material 21 thereof has a five-layered structure in which the first liquid absorbent layer 28 and the second liquid absorbent layer 29 overlap each other in the order of the second liquid absorbent layer/the first liquid absorbent layer/the second liquid absorbent layer/the first liquid absorbent layer/the second liquid absorbent layer.

Comparative Example 1

The absorbent body according to the comparative example 1 was obtained by using the arrangement similar to that in the embodiment 2 except that the second and third dispersing pipes B, C were used to spread the superabsorbent polymer particles and the distance t for these dispersing pipes B, C was set to 25 mm. Evaluation result for the absorbent body 20 obtained in the manner as has been described above was listed in TABLE 1, As the result of the cross-sectional observation for the absorbent body, the state of the core material was as seen from the photo in FIG. 9. Specifically, the superabsorbent polymer particles and the fluff pulp were in a state mixed with each other and it was impossible to confirm the presence of the layered structure.

Comparative Example 2

The absorbent body according to the comparative example 2 was obtained by using the arrangement similar to that in the comparative example 1 except that the distance t was set to 85 mm for the second and third dispersing pipes B, C. Evaluation result for the absorbent body 20 obtained in the manner as has been described above was listed in TABLE 1, As the result of the cross-sectional observation for the absorbent body, the state of the core material was as seen from the photo in FIG. 10 and it was impossible to confirm the presence of the layered structure.

Comparative Example 3

The absorbent body according to the comparative example 3 was obtained by using the arrangement similar to that in the embodiment 5 except that the distance t was set to 22.5 mm for the second dispersing pipe B illustrated in FIG. 3. Evaluation result for the absorbent body 20 obtained in the manner as has been described above was listed in TABLE 1. As the result of the cross-sectional observation for the absorbent body, it was impossible to confirm the presence of the layered structure.

Comparative Example 4

The absorbent body according to the comparative example 4 was obtained by using the arrangement similar to that in the embodiment 6 except that the second and third dispersing pipes B, C illustrated in FIG. 3, of which the respective openings 341 have the dimension M set to 7 mm, respectively, were used and the average flow velocity of the discharged air at the openings was set to 197.7 mm/sec. Evaluation result for the absorbent body 20 obtained in the manner as has been described above was listed in TABLE 1. As the result of the cross-sectional observation for the absorbent body, it was impossible to confirm the presence of the layered structure.

As will be apparent from the evaluation result of the embodiments and the comparative examples listed in TABLE 1, in the embodiments, the core material 21 unexceptionally had the layered structure but, in the comparative example, the core material had no layered structure and the superabsorbent polymer particles and the hydrophilic fibers were in the mixed state over the entire cross-section of the core material. "wicking distance at an angle of 45°" in the embodiments was larger than that in the comparative examples. In the core material 21 according to the embodiments in which the presence of the second liquid absorbent layer 29 formed of the hydrophilic fibers 27 were easily recognized, it may be easily concluded that the colored physiological saline 401 more smoothly diffused in the second liquid absorbent layer 29 than in the core material according to the comparative examples.

same preparative procedure as for the core material according to the comparative example 1. For the core materials according to the comparative examples 5 to 10, used quantity of the superabsorbent polymer particles (SAP) 26 was

TABLE 1

| | Hydrophilic fiber | Mix ratio (%) | Superabsorbent polymer | Mix ratio (%) | Mass per unit area (g/m$^2$) | Thickness of core material (mm) | Used diffuser pipe | Opening size of dispersing pipe R(mm) | Distance from opening to cavity t(mm) | State of peripheral surface | Rate of discharged air (m/sec) | State of cross-section (state of peripheral layer) | Wicking distance at an angle of 45° (mm) |
|---|---|---|---|---|---|---|---|---|---|---|---|---|---|
| Embodiment 1 | NB416 | 45% | UG860D | 55% | 453.6 | 2.4 | A, D | 30 | A, D = 20 | 3 layered (S/P/S) | 46 | layer state | 86.6 |
| Embodiment 2 | NB416 | 45% | UG860D | 55% | 452.0 | 2.4 | B, D | 30 | B = 10 D = 20 | 4 layered (P/S/P/S) | 46 | layer state | 84.0 |
| Embodiment 3 | NB416 | 45% | UG860D | 55% | 455.1 | 2.3 | A, B, D | 30 | A, D = 20 B = 10 | 5 layered (S/P/S/P/S) | 46 | layer state | 80.0 |
| Embodiment 4 | NB416 | 45% | UG860D | 55% | 452.0 | 2.4 | B | 30 | B = 15 | 3 layered (P/S/P) | 46 | layer state | 84.5 |
| Embodiment 5 | NB416 | 45% | UG860D | 55% | 451.3 | 2.4 | B | 30 | B = 20 | 3 layered (P/S/P) | 46 | layer state | 84.8 |
| Embodiment 6 | NB416 | 45% | UG860D | 55% | 450.9 | 2.4 | B, C | 15 | B, C = 10 | 5 layered (P/S/P/S/P) | 92.3 | layer state | 85.0 |
| Comparative example 1 | NB416 | 45% | UG860D | 55% | 454.5 | 2.3 | B, C | 30 | B, C = 25 | mixed layer | 46 | mixed state | 68.6 |
| Comparative example 2 | NB416 | 45% | UG860D | 55% | 456.3 | 2.3 | B, C | 30 | B, C = 85 | mixed layer | 46 | mixed state | 69.6 |
| Comparative example 3 | NB416 | 45% | UG860D | 55% | 454.4 | 2.4 | B | 30 | B, C = 22.5 | mixed layer | 46 | mixed state | 67.2 |
| Comparative example 4 | NB416 | 45% | UG860D | 55% | 454.8 | 2.4 | B, C | 7 | B, C = 10 | mixed layer | 197.7 | mixed state | 67.0 |

(Note :)

{ P: first liquid absorbent layer
  S: second liquid absorbent layer

Configuration of Core Material, Observation and Evaluation of Performance Thereof (2)

Keeping the total mass of the superabsorbent polymer particles 26 and the hydrophilic fibers 27 at the level of 650 g/m$^2$ but varying the mass ratio between the superabsorbent polymer particles (SAP) 26 and the hydrophilic fibers 27, the core materials 21 according to embodiments 7 to 19 each having the dimension L=300 mm, W=100 mm were obtained with use of the same preparative procedure as for the core material 21 according to the embodiment 3. For the core materials according to the embodiments 7 to 12, used quantity of the superabsorbent polymer particles 26 was fixed at 250 g/m$^2$ and used quantity of the hydrophilic fibers was varied between 150 to 400 g/m$^2$. The core materials according to comparative examples each having the dimension L=300 mm, W=100 mm were obtained with use of the fixed at 250 g/m$^2$ and used quantity of the hydrophilic fibers was varied. In the case of the core materials according to comparative examples 11 to 17, used quantity of the hydrophilic fibers 27 was fixed at 250 g/m$^2$ and used quantity of the superabsorbent polymer particles 26 was varied.

For the core materials 21 according to these embodiments and the core materials according to these comparative examples, the wicking distance at an angle of 45°, the absorption time and the rewet quantity were evaluated with use of methods as described below. Especially for the core material according to the embodiment 15, X-ray CT photo was took by following a procedure as described below and, on the basis of this photo, a volume fraction of the superabsorbent polymer particles 26 in the first liquid absorbent layer 28 was measured.

TABLE 2

| Quantity of superabsorbent polymer used 250 g/m$^2$ Testpiece name | Quantity of hydrophilic fiber g/m$^2$ | Testpiece Mass per unit area g | Testpiece Thickness mm | Absorption time Liquid supplied 80 ml s | Absorption time Liquid supplied 160 ml s | Absorption time Liquid supplied 240 ml s | Rewet quantity Liquid supplied 80 ml g | Rewet quantity Liquid supplied 160 ml g | Rewet quantity Liquid supplied 240 ml g | Wicking distance at an angle of 45° | Testpiece Mass per unit area g | Testpiece Thickness mm | Observation time for wicking distance 1 min mm | Observation time for wicking distance 5 min mm | Observation time for wicking distance 10 min mm |
|---|---|---|---|---|---|---|---|---|---|---|---|---|---|---|---|
| Embodiment 7 | 150 | 13.27 | 1.48 | 27.03 | 16.1 | 18.64 | 0.95 | 9.49 | 41.08 | | 13.12 | 1.4 | 110 | 145 | 160 |
| Embodiment 8 | 200 | 15.11 | 1.59 | 25.2 | 14.96 | 16.38 | 0.46 | 3.8 | 17.69 | | 15.31 | 1.5 | 105 | 140 | 160 |
| Embodiment 9 | 250 | 17.15 | 1.54 | 23.15 | 15.65 | 15.1 | 0.28 | 2.36 | 10.2 | | 17.16 | 1.65 | 100 | 135 | 165 |
| Embodiment 10 | 300 | 18.67 | 1.8 | 20.5 | 14.75 | 14.31 | 0.22 | 1.64 | 5.59 | | 18.66 | 1.84 | 105 | 130 | 150 |
| Embodiment 11 | 350 | 20.6 | 1.8 | 19.1 | 14.73 | 14.42 | 0.21 | 1.33 | 4.41 | | 20.5 | 1.85 | 105 | 130 | 155 |
| Embodiment 12 | 400 | 22.39 | 1.91 | 19.01 | 14.5 | 13.96 | 0.18 | 1.17 | 3.69 | | 22.56 | 2.1 | 105 | 140 | 155 |
| Comparative example 5 | 150 | 13.3 | 1.54 | 28.59 | 18.49 | 23.42 | 4.63 | 42.39 | 52.34 | | 12.93 | 1.45 | 105 | 140 | 155 |

TABLE 2-continued

| Quantity of superabsorbent polymer used 250 g/m² Testpiece name | Quantity of hydrophilic fiber g/m² | Testpiece Mass per unit area g | Thickness mm | Absorption time Liquid supplied 80 ml s | 160 ml s | 240 ml s | Rewet quantity Liquid supplied 80 ml g | 160 ml g | 240 ml g | Wicking distance at an angle of 45° | Testpiece Mass per unit area g | Thickness mm | Observation time for wicking distance 1 min mm | 5 min mm | 10 min mm |
|---|---|---|---|---|---|---|---|---|---|---|---|---|---|---|---|
| Comparative example 6 | 200 | 14.85 | 1.71 | 24.44 | 17.31 | 21.26 | 1.18 | 31.27 | 43.92 | | 15.09 | 1.65 | 100 | 140 | 155 |
| Comparative example 7 | 250 | 16.42 | 1.81 | 26.31 | 16.13 | 20.41 | 0.6 | 28.31 | 46.66 | | 16.76 | 1.75 | 95 | 130 | 140 |
| Comparative example 8 | 300 | 18.32 | 2.02 | 23.57 | 14.81 | 17.96 | 0.3 | 19.18 | 44.43 | | 18.22 | 1.8 | 80 | 110 | 125 |
| Comparative example 9 | 350 | 19.32 | 2.08 | 23.95 | 15.5 | | 0.19 | 13.56 | 39.84 | | 19.83 | 2 | 85 | 110 | 130 |
| Comparative example 10 | 400 | 21.25 | 2.3 | 20.8 | 14.61 | 16.59 | 0.25 | 10.48 | 37.69 | | 21.27 | 2 | 85 | 110 | 125 |

Pulp 50-400 g/m²
SAP 250 g/m²

TABLE 3

| Quantity of hydrophilic fiber 250 g/m² Testpiece name | Quantity of hydrophilic fiber g/m² | Testpiece Mass per unit area g | Thickness mm | Absorption time Liquid supplied 80 ml s | 160 ml s | 240 ml s | Rewet quantity Liquid supplied 80 ml g | 160 ml g | 240 ml g | Wicking distance at an angle of 45° | Testpiece Mass per unit area g | Thickness mm | Observation time for wicking distance 1 min mm | 5 min mm | 10 min mm |
|---|---|---|---|---|---|---|---|---|---|---|---|---|---|---|---|
| Embodiment 13 | 150 | 14.28 | 1.3 | 24.33 | 15.54 | 15.34 | 0.33 | 2.97 | 16.75 | | 14.38 | 1.4 | 95 | 130 | 145 |
| Embodiment 14 | 175 | 15.11 | 1.51 | 24.7 | 14.65 | 13.99 | 0.24 | 2.76 | 17.29 | | 15.15 | 1.5 | 100 | 130 | 150 |
| Embodiment 15 | 200 | 15.01 | 1.45 | 22.3 | 14 | 13.84 | 0.38 | 3.31 | 15.94 | | 15.46 | 1.5 | 100 | 135 | 155 |
| Embodiment 16 | 225 | 16.58 | 1.43 | 22.89 | 13.51 | 14.04 | 0.36 | 3.23 | 17.54 | | 15.12 | 1.5 | 105 | 145 | 160 |
| Embodiment 17 | 250 | 17.15 | 1.54 | 23.15 | 15.65 | 15.1 | 0.28 | 2.36 | 10.2 | | 17.16 | 1.65 | 100 | 135 | 165 |
| Embodiment 18 | 300 | 18.11 | 1.75 | 21.79 | 14.57 | 15.2 | 0.33 | 2.49 | 9.62 | | 18.06 | 2 | 110 | 145 | 170 |
| Embodiment 19 | 350 | 19.34 | 1.9 | 21.26 | 14.1 | 14.27 | 0.28 | 2.09 | 8.1 | | 19.33 | 2 | 120 | 160 | 185 |
| Comparative example 11 | 150 | 13.86 | 1.6 | 29.22 | 19.06 | 23.81 | 0.45 | 23.24 | 43.11 | | 13.82 | 1.4 | 75 | 100 | 120 |
| Comparative example 12 | 175 | 14.23 | 1.5 | 27.95 | 18.26 | 21.46 | 0.6 | 24.46 | 42.55 | | 14.7 | 1.6 | 85 | 115 | 125 |
| Comparative example 13 | 200 | 15.66 | 1.74 | 26.53 | 17.03 | 20.23 | 0.52 | 23.72 | 43.26 | | 15.7 | 1.6 | 100 | 125 | 140 |
| Comparative example 14 | 225 | 16.05 | 1.79 | 27.67 | 16.08 | 19.73 | 0.69 | 26.35 | 48.36 | | 15.85 | 1.8 | 90 | 110 | 130 |
| Comparative example 15 | 250 | 16.42 | 1.81 | 26.31 | 16.13 | 20.41 | 0.6 | 28.31 | 46.66 | | 16.76 | 1.75 | 95 | 130 | 140 |
| Comparative example 16 | 300 | 17.33 | 2.1 | 21.77 | 14.54 | 17.73 | 0.84 | 29.97 | 46.83 | | 17.8 | 2 | 95 | 120 | 140 |
| Comparative example 17 | 350 | 19.03 | 2.3 | 20.93 | 13.52 | 15.69 | 0.56 | 30.19 | 49.33 | | 19.07 | 2.3 | 95 | 130 | 145 |

Pulp 250 g/m²
SAP 150-350 g/m²

1. Wicking Distance at an Angle of 45°

(1) The same procedure as described in "4. Wicking distance at an angle of 45°" in "Configuration of core material, observation and evaluation of performance thereof (1)" was followed to measure the wicking distances (mm) at an angle of 45° in the core materials according to the embodiments and to the comparative examples. In this regard, the times for observation after start of testing were set to 1, 5, 10 minutes. Besides, the step d having been adopted at "4. wicking distance at an angle of 45°" was not adopted and the test pieces were prepared from the core material having been kept in the room at 23° C., R. H. of 60% for 48 hours or longer and these test pieces were set on the testing equipment 400.

2. Absorption Time (1) The test piece was placed on an acrylic plastic plate.
(2) An acrylic plastic cylinder having outer diameter of 67 mm, inner diameter of 60 mm, height of 50 mm and mass of 60 g was placed on a center of upper surface of the test piece.
(3) A burette was set so that a lower end of the burette may be positioned 10 mm above the upper surface of the test piece in a central portion of the cylinder.
(4) The burette was filled with artificial urine and dropping of artificial urine to the test piece at a rate of 80 ml/10 sec was started.

Artificial urine: 200 g of urea, 80 g of sodium chloride, 8 g of 7 hydrate of magnesium sulfate, 3 g of 2 hydrate of calcium chloride and 1 g of dye (Blue No. 1) mixed in 10 kg of ion-exchanged water under sufficient agitation was used as the artificial urine.

(5) Concurrently with start of the artificial urine dropping, a stop-watch is started up and the inside of the cylinder was observed after 80 ml of artificial urine has been dropped and also the time elapse until the artificial urine was absorbed by the test piece was measured.

(6) An average value of the time elapses measured on five test pieces is calculated and this average value was adopted as "absorption time" versus the liquid supplied quantity of 80 ml.

(7) After 10 minutes from start of the artificial urine dropping, the steps (4) to (6) were repeated to drop additional 80 ml of the artificial urine and to measure "absorption time" for liquid supply quantity of 160 ml.

(8) After 20 minutes from start of the artificial urine dropping, the steps (4) to (6) were repeated to drop additional 80 ml of the artificial urine and to measure "absorption time" for liquid supply quantity of 240 ml.

3. Rewet Quantity (1) 80 ml of the artificial urine was dropped onto the test piece by following the same procedure as that followed in the measurement of "2. absorption time" (first dropping of the artificial urine).

(2) Five minutes after dropping of the artificial urine has been started, the mass measured filter paper (ADVANTEC No. 2, 100 mm×100 mm manufactured by ADVANTEC CO., LTD.) (mass A) was placed on a central region of the test piece and a weight of 3.5 kg/100 cm$^2$ was placed on this filter paper. 3 minutes after the weight was removed and a mass of the filter paper (mass B) was measured.

(3) A difference between the mass B and the mass A was calculated and adopted as "rewet quantity" versus 80 ml as the liquid supply quantity.

(4) 10 minutes after the first dropping of the artificial urine had been started, 80 ml of the artificial urine was additionally dropped onto the test piece (second dropping of the artificial urine).

(5) 5 minutes after the second dropping of the artificial urine had been started, the mass measured filter paper (mass C) was placed on the central region of the test piece and a weight of 3.5 kg/100 cm$^2$ was placed on the filter paper. 3 minutes after, the weight was removed and a mass (mass D) of the filter paper was measured.

(6) A difference between the mass D and the mass C was calculated and this difference was adopted as "rewet quantity" versus 160 ml of liquid feed quantity.

(7) 10 minutes after the second dropping of the artificial urine had been started, 80 ml of the artificial urine was additionally dropped onto the test piece (third dropping of the artificial urine).

(8) 5 minutes after the third dropping of the artificial urine had been started, the mass measured filter paper (mass E) was placed on the central region of the test piece and a weight of 3.5 kg/100 cm$^2$ was placed on the filter paper. 3 minutes after, the weight was removed and a mass (mass F) of the filter paper was measured.

(9) A difference between the mass F and the mass E was calculated and adopted as "rewet quantity" versus 240 ml as the liquid feed quantity.

4. Volume Fraction of Superabsorbent Polymer Particles (1) The upper and lower cover sheets 22a, 22b were peeled off from the absorbent body 20 according to the embodiment 15 having the first liquid absorbent layer 28 and the second liquid absorbent layer 29 to obtain the core material 21 and small pieces of this core material 21 were used as the test pieces for measurement.

(2) For measurement of the volume fraction, a stereoimage was prepared from a cross-sectional image obtained by X-ray CT with use of an analysis soft, this stereoimage was binarized to divide the entire core material 21 into a portion in which the superabsorbent polymer particles are present and a portion in which the superabsorbent polymer particles are not present (portion occupied by the hydrophilic fibers 27 and gaps) thereby the core material 21 was divided into the first liquid absorbent layer 28 and the second liquid absorbent layer 29 in the thickness direction, and a volume fractions of the superabsorbent polymer particles 26 in each layer were measured.

Figure 17:
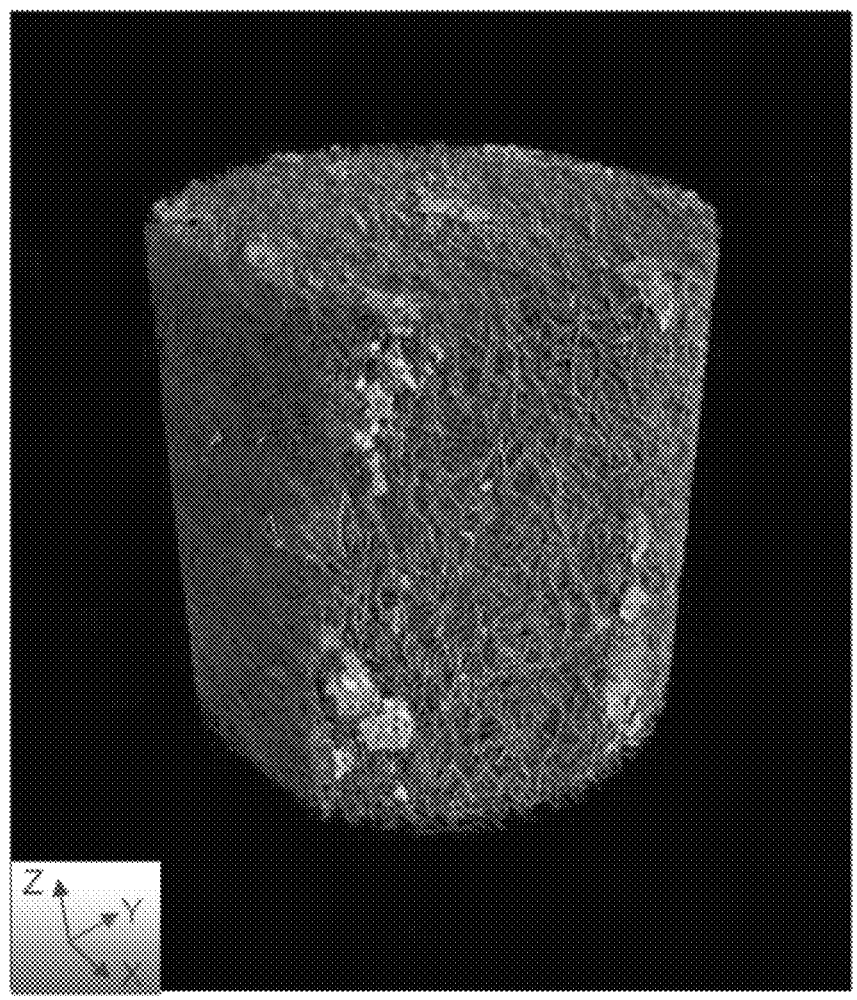
FIG. 17 is one example of X-ray CT photo showing a stereo image of a test piece obtained from core material.
Figure 18:
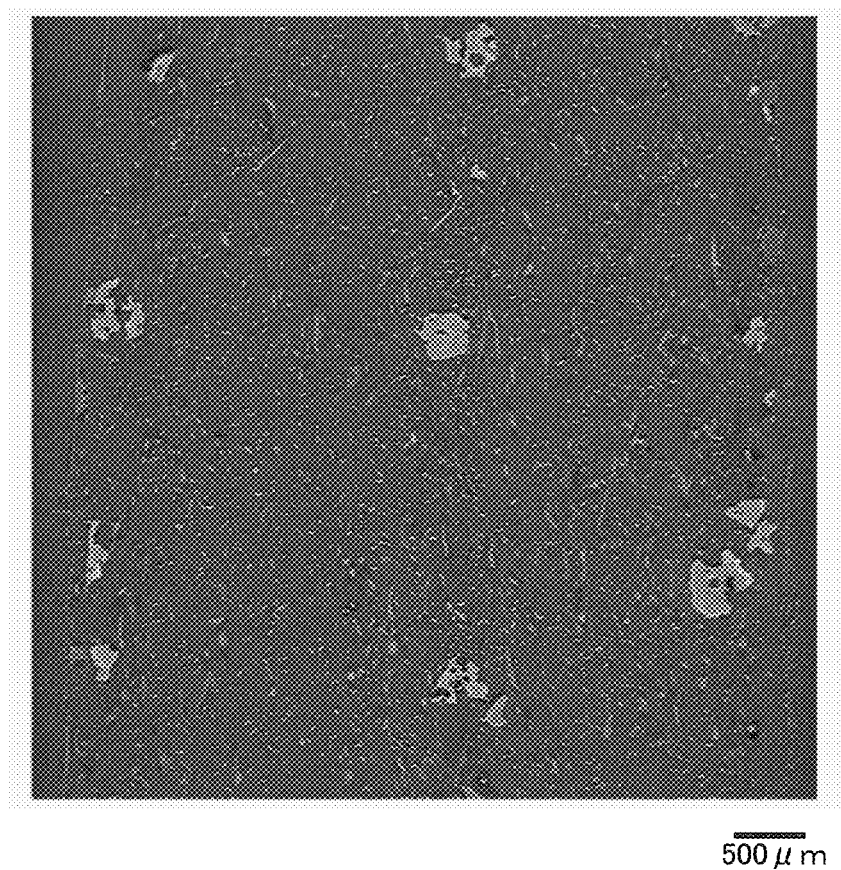
FIG. 18 is an X-ray CT photo showing a tomographic image of Y-Z cross-sectional surface of the test piece shown in FIG. 17.

(3) FIGS. 17, 18, 19 exemplarily show the X-ray CT photos of the core material. FIG. 17 shows a stereoimage of the test piece as observed obliquely from above, in which the directions corresponding to the transverse direction G, the longitudinal direction F and the thickness direction H, respectively, are indicated by X, Z and Y. FIG. 18 shows the cross-sectional image taken along the YZ cross-sectional surface in FIG. 17 and FIG. 19 is a stereoimage taken along the YZ cross-sectional surface. In FIG. 19, the superabsorbent polymer particles 26, the hydrophilic fibers 27, the first liquid absorbent layer 28 and the second liquid absorbent layer 29 visually recognized. A tangent line 50 coming in contact in the thickness direction Y with the superabsorbent polymer particles 26 and a line 50a coming in contact with the surface of the core material 21 may be drawn as illustrated to obtain the first liquid absorbent layer 28 and the second liquid absorbent layer 29. In this way, it is possible to identify the first liquid absorbent layer 28 and the second liquid absorbent layer 29 from each other with use of the X-ray CT photos.

(4) Equipment and Measuring Condition Will be Described Below.

Used Instruments 3D measuring A-ray CT equipment: TDM1000-IS/SP (manufactured by Yamato Scientific Co., Ltd.)

3D Volume Lendering Soft: VG-StudioMAX (manufactured by NVS)

Measurement Condition

Tube voltage: 40 kV

Tube current: 20 μA

Number of pixels: 1024×1024 pixels

Size of visual field: diameter 5.5 mm×depth 5.5 mm

Figure 11:
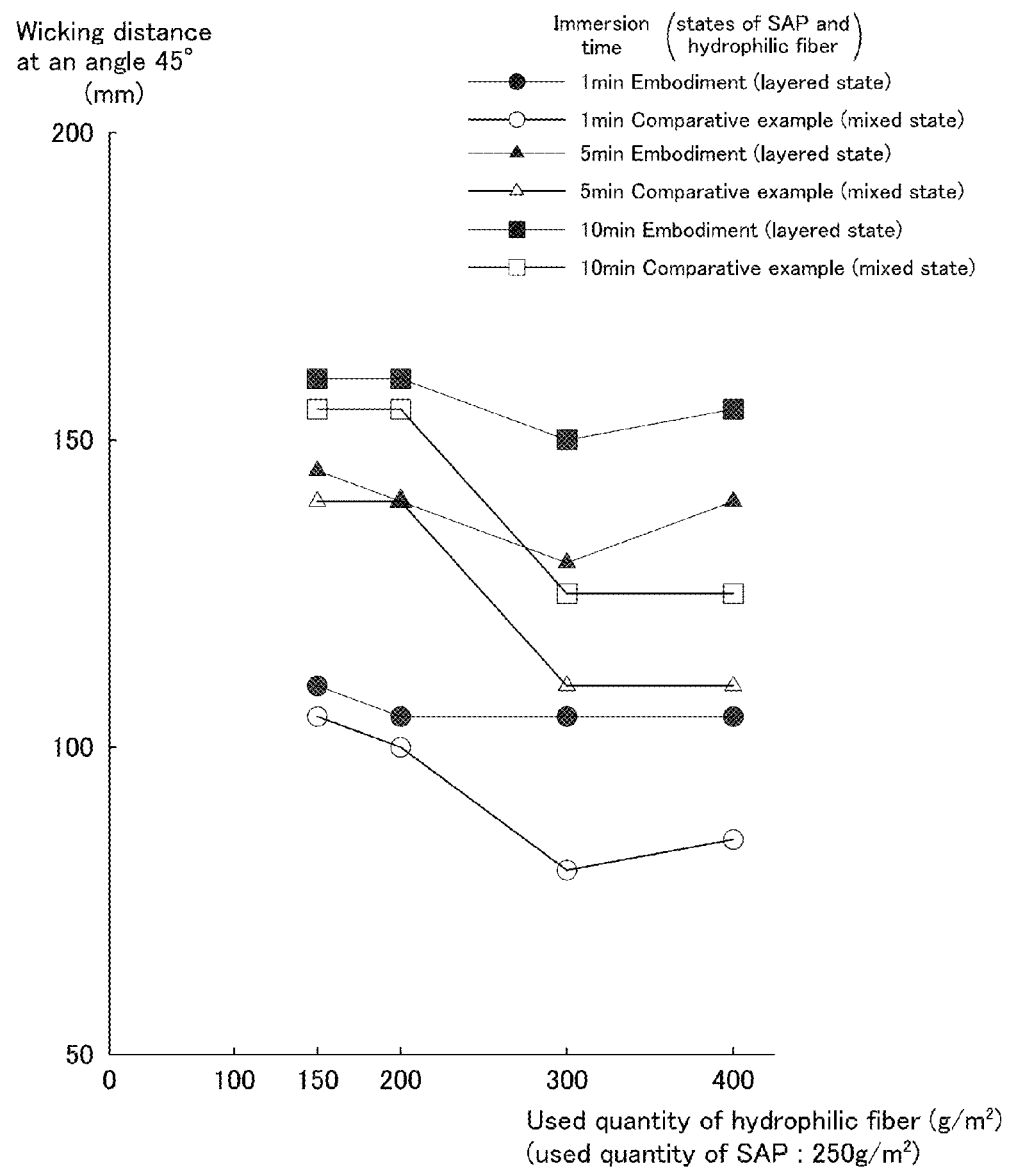
FIG. 11 is a graphic diagram plotting a relationship between used quantity of hydrophilic fibers and wicking distance at an angle of 45° listed in TABLE 2.
Figure 12:
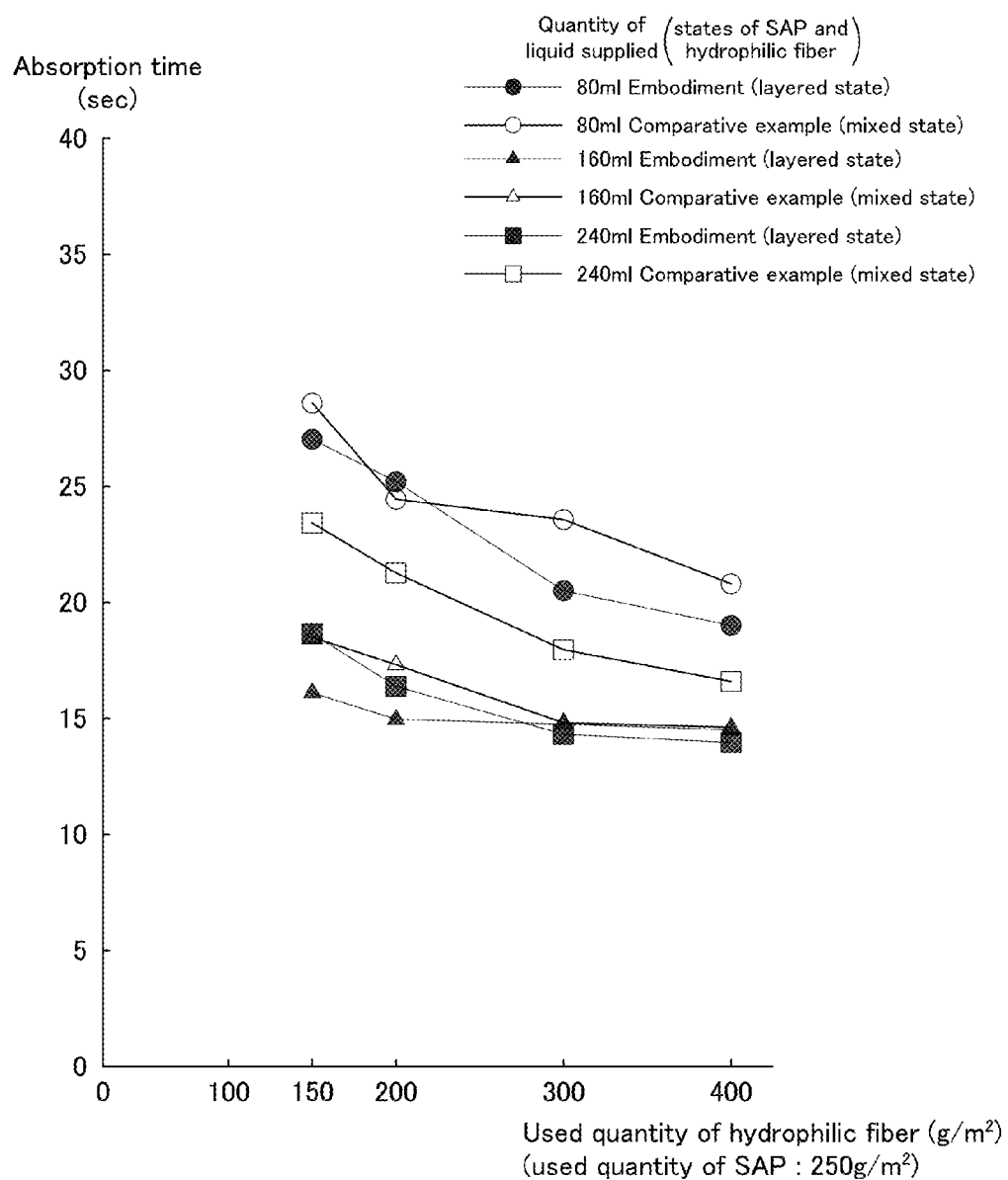
FIG. 12 is a graphic diagram plotting a relationship between used quantity of hydrophilic fibers and absorption time listed in TABLE 2.
Figure 13:
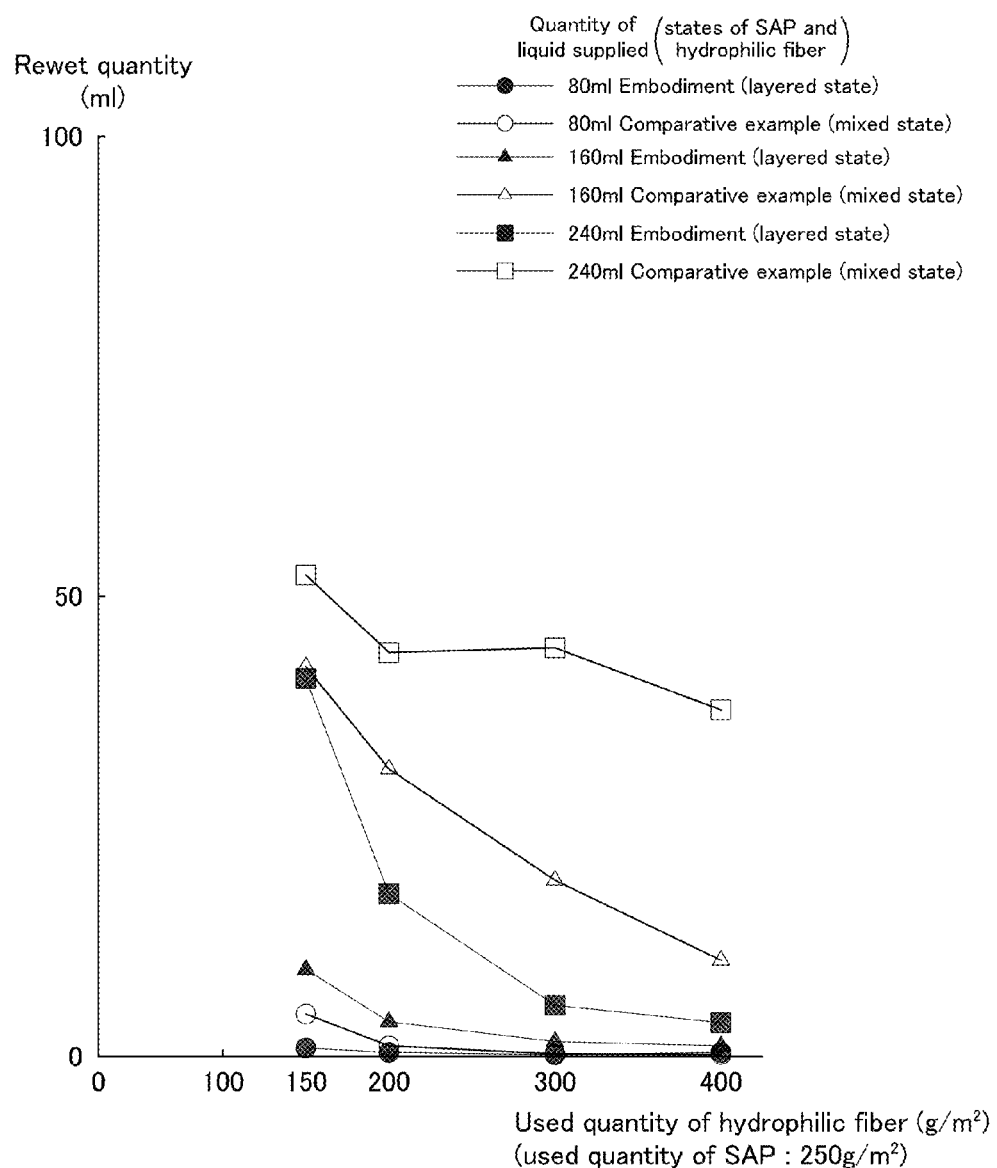
FIG. 13 is a graphic diagram plotting a relationship between used quantity of hydrophilic fibers and rewet quantity listed in TABLE 2.

FIGS. 11, 12 and 13 graphically illustrate the measurement results of "wicking distance at an angle of 45°", "absorption time" and "rewet quantity" listed in TABLE 2. In FIGS. 11, 12 and 13, the used quantity of the superabsorbent polymer particles (SAP) 26 is fixed to 250 g/m$^2$ and the used quantity of the hydrophilic fibers 27 is varied in a range between 150 to 400 g/m$^2$.

Figure 14:
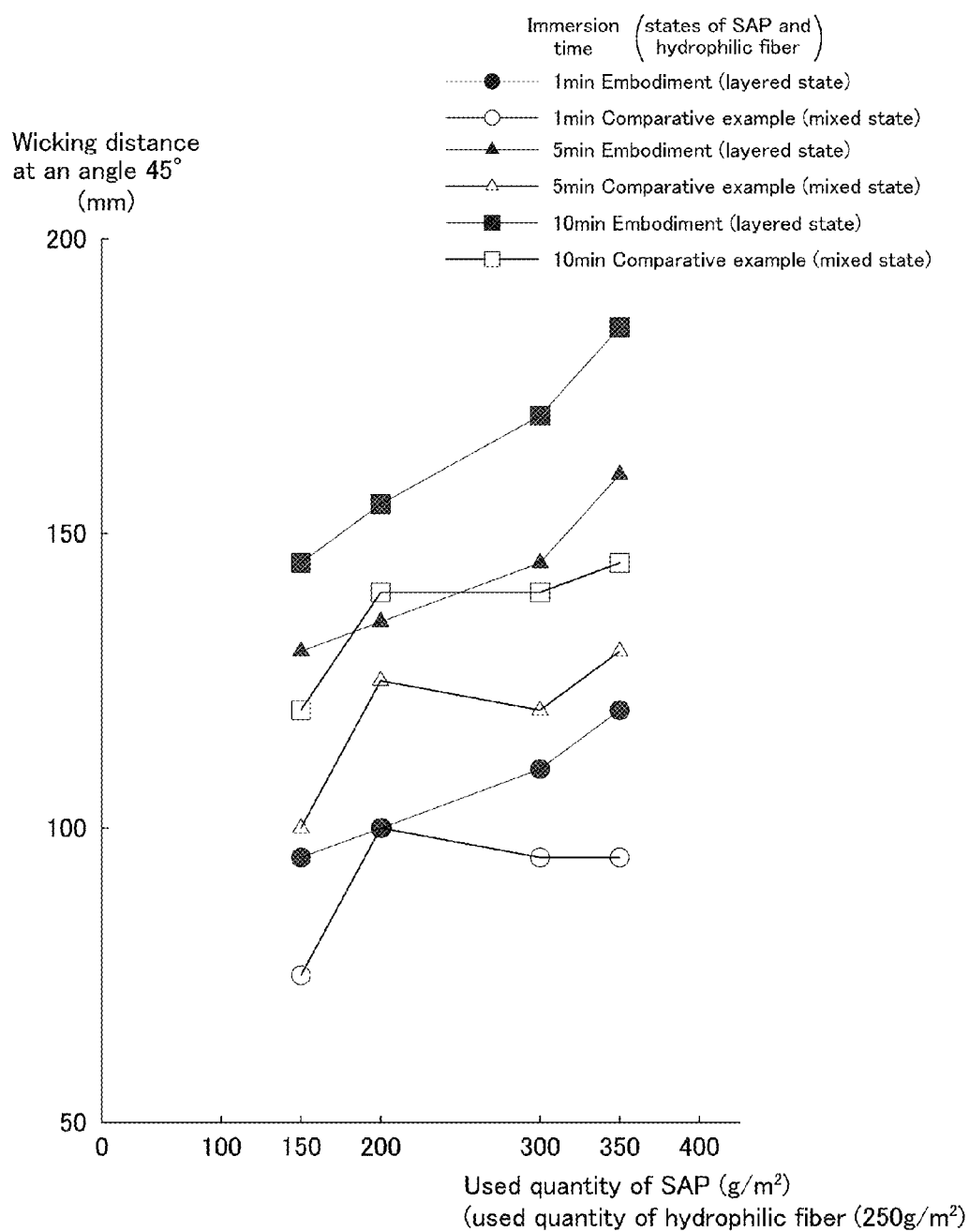
FIG. 14 is a graphic diagram plotting a relationship between used quantity of superabsorbent polymer particles (SAP) and wicking distance at an angle of 45° listed in TABLE 3.
Figure 15:
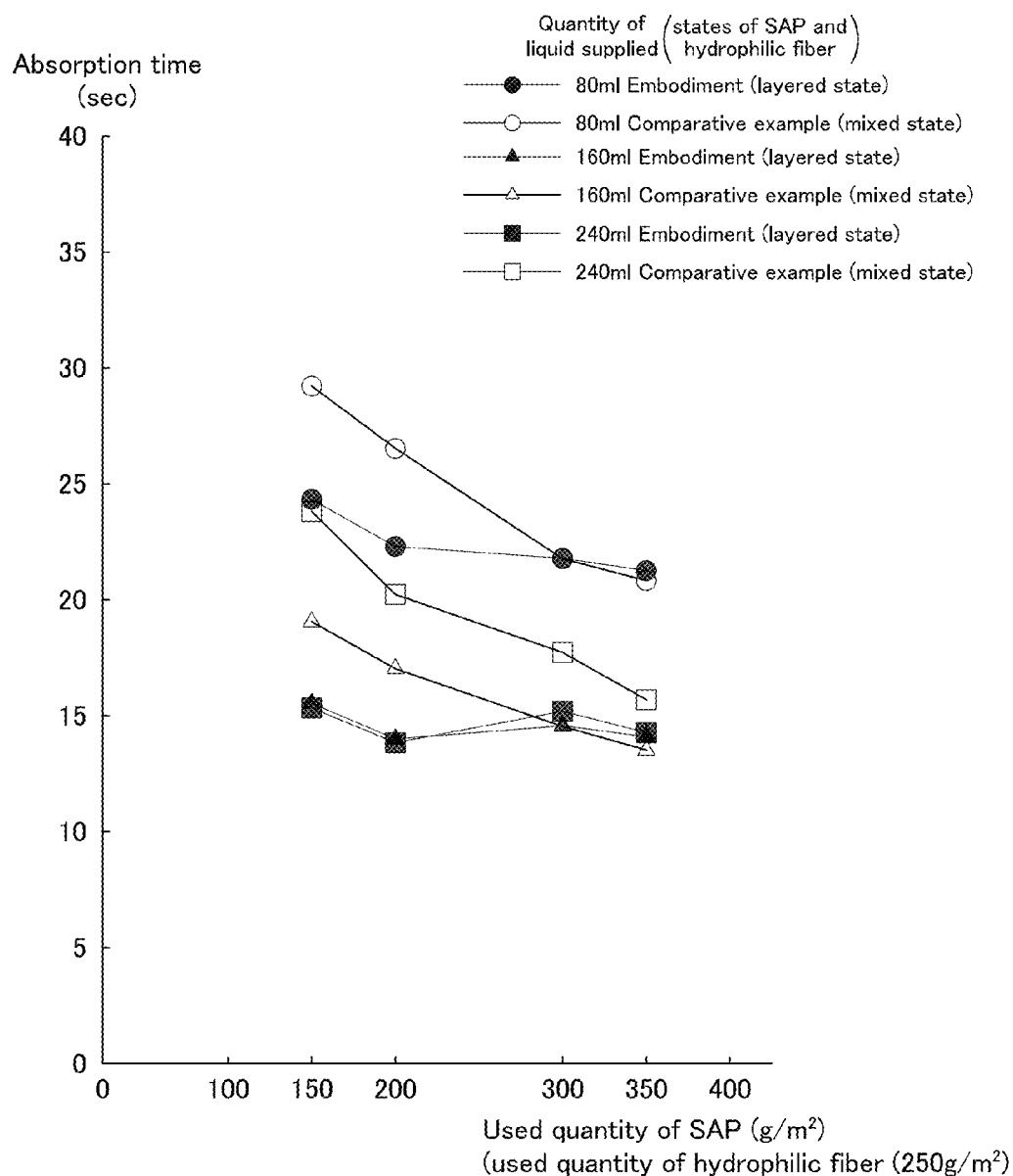
FIG. 15 is a graphic diagram plotting a relationship between used quantity of superabsorbent polymer particles (SAP) and absorption time listed in TABLE 3.
Figure 16:
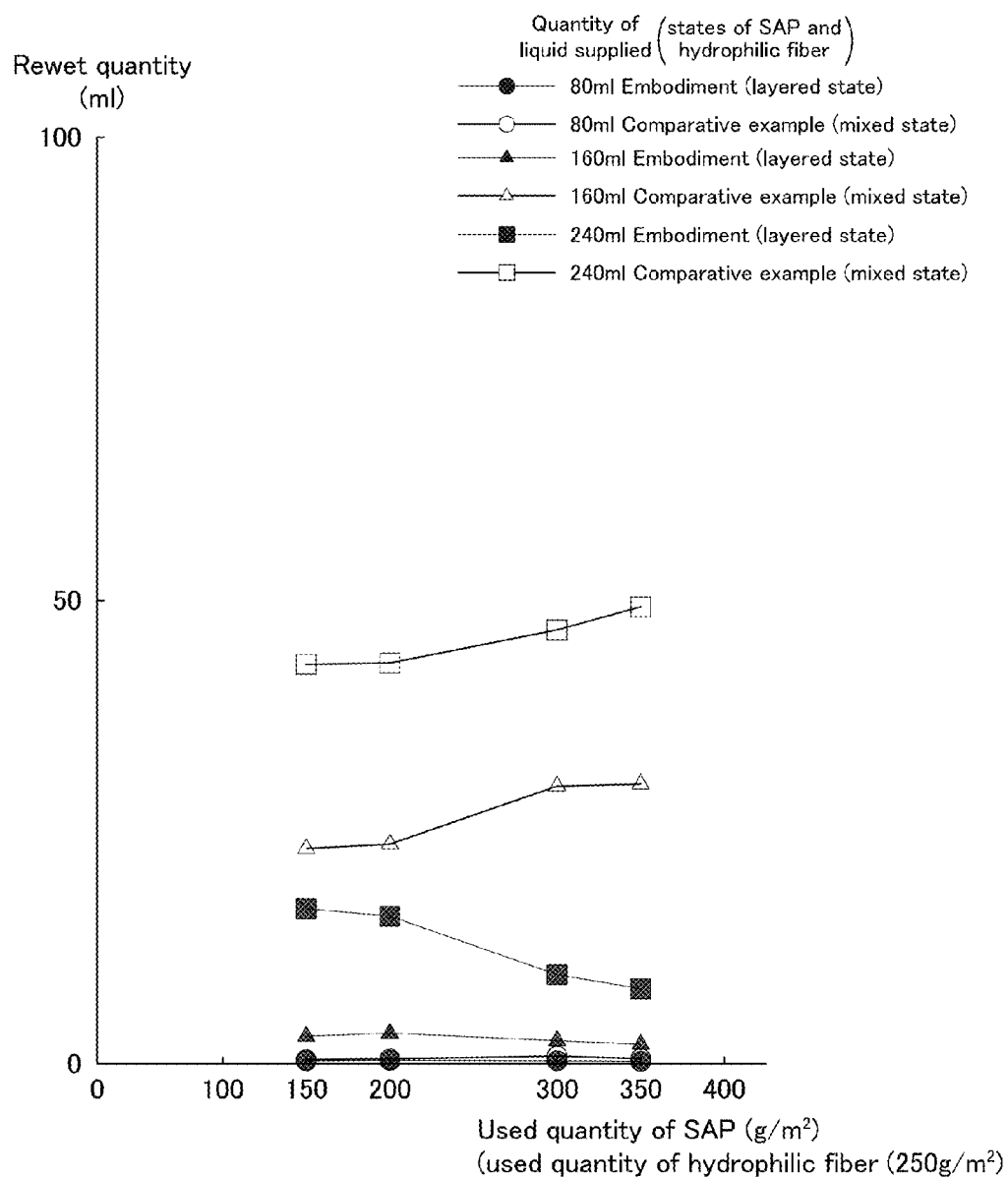
FIG. 16 is a graphic diagram plotting a relationship between used quantity of superabsorbent polymer particles (SAP) and rewet quantity listed in TABLE 3.

FIGS. 14, 15 and 16 graphically illustrate the measurement results listed in TABLE 3. In FIGS. 14, 15 and 16, the used quantity of the hydrophilic fibers 27 in the core material is fixed to 250 g/m$^2$ and the used quantity of the superabsorbent polymer particles 26 is varied in a range between 150 to 350 g/m$^2$.

Referring to FIGS. 11 to 16, the core material 21 having the layered structure was compared with a comparative core material having the superabsorbent polymer particles and the hydrophilic fibers are in mixed state in the entire region thereof to obtain the result as described below.

a. Concerning "wicking distance at an angle of 45°", irrespectively of the used quantities of the superabsorbent polymer particles and the hydrophilic fibers, the performance of the core material 21 was superior to that of the comparative example. Such difference between the core material 21 and the core material according to the comparative example is recognized also between the embodiments 1 to 6 and the comparative examples 1 to 4 listed in TABLE 1.

b. Concerning "absorption time", when the used quantity of the hydrophilic fibers 27 is 150 g/m$^2$ or more, more preferably 200 g/m$^2$ or more, the performance of the core material 21 is likely superior to the performance of the core material according to the comparative examples. When the used quantity of the superabsorbent polymer particles 26 is 350 g/m² or more, strictly 300 g/m² or more, there was a possibility that the performance of the core material 21 might become inferior to the core material according to the comparative examples.

c. Concerning "rewet quantity", the performance of both the core material 21 and the core material according to the comparative examples is proportionately improved, i.e., the rewet quantity is decreased when the quantities of both the superabsorbent polymer particles 26 and the hydrophilic fibers 27 are increased.

The volume fraction of the superabsorbent polymer particles 26 in each of the first liquid absorbent layers 28 in the core material 28 according to the example 15 was in a range of 2.4 to 7%.

Various embodiments in accordance with the disclosure of the first aspect of the present invention may be arranged into one or more of the features as follow:

An absorbent body for an absorbent article including an absorbent core material containing therein hydrophilic fibers and superabsorbent polymer particles and covered with at least partially liquid-permeable cover sheet, wherein:

the core material has amass per unit area of 650 g/m² or less and contains the hydrophilic fibers in a range of 150 to 400 g/m² and the superabsorbent polymer particles in a range of 150 to 350 g/m² wherein a first liquid absorbent layer in which the hydrophilic fibers and the superabsorbent polymer particles are mixed with one another and a second liquid absorbent layer containing the hydrophilic fibers but not containing the superabsorbent polymer particles overlap each other in a thickness direction of the core material and the hydrophilic fibers are in contact with each other between the first liquid absorbent layer and the second liquid absorbent layer.

The present disclosure of the first aspect of the present invention may include at least the embodiments, which may be taken in isolation from or in combination with one another.

(1) The first liquid absorbent layer and the second liquid absorbent layer can be distinguished from each other by X-ray CT observation of the core material.

(2) The first liquid absorbent layer and the second liquid absorbent layer overlap with each other so as to forma structure including at least three layers.

(3) The first liquid absorbent layer is formed of one to three layers and the second liquid absorbent layer is formed of one or two layers.

(4) The first liquid absorbent layer is formed on one of a top portion and a bottom portion of the core material as viewed in the thickness direction.

(5) The second liquid absorbent layer is formed on one of the top portion and the bottom portion of the core material as viewed in the thickness direction.

(6) The core material has, in addition to the thickness direction, a longitudinal direction and a transverse direction being orthogonal to each other and the first liquid absorbent layer and the second liquid absorbent layer extend to at least one pair of opposite edge portions of the core material having a pair of opposite edge portions defined by end edges thereof opposite in the longitudinal direction and a pair of edge portions defined by side edges thereof opposite in the transverse direction.

Various embodiments in accordance with the disclosure of the second aspect of the present invention may be arranged into one or more of the features as follow:

A method for producing an absorbent body for an absorbent article including an absorbent core material containing therein hydrophilic fibers and superabsorbent polymer particles and covered with at least partially liquid-permeable cover sheet, wherein:

in a step of forming a first liquid absorbent layer containing the hydrophilic fibers and the superabsorbent polymer particles in a mixed state and a second liquid absorbent layer containing the hydrophilic fibers but none of the superabsorbent polymer particles so that these two liquid absorbent layers may overlap with each other on a support running in a machine direction, the hydrophilic fibers are dispersed toward the support within a chamber partially covering the support and the superabsorbent polymer particles are dispersed toward the support from an opening of a dispersing pipe set at least one of inside and outside the chamber wherein a distance dimension between the dispersing pipe set inside the chamber is in a range of 5 to 20 mm and a distance dimension between the dispersing pipe set outside the chamber and the support is in a range of 5 to 100 mm.

The present disclosure of the first aspect of the present invention may include at least the embodiments, which may be taken in isolation from or in combination with one another.

(1) The dispersing pipe set outside the chamber is set at least one of upstream and downstream in the machine direction of the chamber.

(2) An average flow velocity of discharged air at the opening of the dispersing pipe set inside the chamber is less than 100 m/sec.

(3) A part in the machine direction of the support is defined by a rotary drum rotating in the machine direction within the chamber and a peripheral surface of the drum is formed with a continuous cavity over a entire circumferential range so that the hydrophilic fibers and the superabsorbent polymer particles may be dispersed and deposited in this cavity.

(4) A part in the machine direction of the support is defined by a rotary drum rotating in the machine direction within the chamber and a peripheral surface of the drum is formed with a series of cavities over an entire circumferential range so that the hydrophilic fibers and the superabsorbent polymer particles may be dispersed and deposited in these cavities, and the plurality of cavities are arranged at regular intervals in a circumferential direction and a distance between a pair of the cavities adjacent in the circumferential direction is in a range of 5 to 10 mm.

REFERENCE SIGNS LIST 1 absorbent article (disposable diaper)
2 first surface (topsheet)
3 second surface (backsheet)
20 absorbent body
21 core material
22 cover sheet
22a cover sheet (upper cover sheet)
22b cover sheet (lower cover sheet)
26 superabsorbent polymer particles
27 hydrophilic fibers
28 first liquid-absorbent layer
29 second liquid-absorbent layer
31 first layer
32 second layer
33 third layer
36 edge portions (first edge portions)
37 edge portions (second edge portions)
38 top portion
39 bottom portion
323 support (drum)

324 cavities
325 chamber
341 opening
A dispersing pipe
B dispersing pipe
C dispersing pipe
F longitudinal direction
G transverse direction
H thickness direction

The invention claimed is:

1. A method for producing an absorbent body for an absorbent article including the absorbent core material containing therein hydrophilic fibers and superabsorbent polymer particles and covered with at least partially liquid-permeable cover sheet, wherein:

in a step of forming a first liquid absorbent layer containing the hydrophilic fibers and the superabsorbent polymer particles in a mixed state and a second liquid absorbent layer containing the hydrophilic fibers but none of the superabsorbent polymer particles so that these two liquid absorbent layers overlap with each other on a support running in a machine direction, the hydrophilic fibers are dispersed toward the support within a chamber partially covering the support and the superabsorbent polymer particles are dispersed toward the support from an opening of a dispersing pipe set at least one of inside and outside the chamber wherein a distance dimension between the dispersing pipe set inside the chamber and the support is in a range of 5 to 20 mm and a distance dimension between the dispersing pipe set outside the chamber and the support is in a range of 5 to 100 mm; and the dispersing pipe set outside the chamber is set at least one of upstream and downstream in the machine direction of the chamber.

2. The method for producing the absorbent body according to claim 1, wherein an average flow velocity of discharged air at the opening of the dispersing pipe set inside the chamber is less than 100 m/sec.

3. The method for producing the absorbent body according to claim 1, wherein a part in the machine direction of the support is defined by a rotary drum rotating in the machine direction within the chamber and a peripheral surface of the drum is formed with a cavity over an entire circumferential range so that the hydrophilic fibers and the superabsorbent polymer particles are dispersed and deposited in this cavity.

4. The method for producing the absorbent body according to claim 1, wherein a part in the machine direction of the support is defined by a rotary drum rotating in the machine direction within the chamber and a peripheral surface of the drum is formed with a series of cavities over an entire circumferential range so that the hydrophilic fibers and the superabsorbent polymer particles are dispersed and deposited in these cavities and wherein the plurality of cavities are arranged at regular intervals in a circumferential direction and a distance between a pair of the cavities adjacent in the circumferential direction is in a range of 5 to 10 mm.

* * * * *